United States Patent
Alperin

(10) Patent No.: US 12,431,223 B1
(45) Date of Patent: Sep. 30, 2025

(54) APPARATUS AND METHODS FOR MATCHING USER DATA WITH THIRD-PARTY DATA STRUCTURES

(71) Applicant: SurvivorNet, Inc., New York, NY (US)

(72) Inventor: Steven David Alperin, New York, NY (US)

(73) Assignee: SurvivorNet, Inc., New York, NY (US)

( * ) Notice: Subject to any disclaimer, the term of this patent is extended or adjusted under 35 U.S.C. 154(b) by 0 days.

(21) Appl. No.: 19/057,446

(22) Filed: Feb. 19, 2025

(51) Int. Cl.
G16H 10/20 (2018.01)
G06F 16/242 (2019.01)

(52) U.S. Cl.
CPC ........... *G16H 10/20* (2018.01); *G06F 16/242* (2019.01)

(58) Field of Classification Search
CPC .............................. G16H 10/20; G06F 16/242
See application file for complete search history.

(56) References Cited

U.S. PATENT DOCUMENTS

| | | | |
|---|---|---|---|
| 7,761,423 B1 * | 7/2010 | Cohen | G06Q 30/02 707/706 |
| 9,721,026 B1 * | 8/2017 | Tober | G06F 16/951 |
| 11,158,402 B2 | 10/2021 | Clark et al. | |
| 2022/0319697 A1 | 10/2022 | Morris et al. | |
| 2023/0274809 A1 * | 8/2023 | Dimitrova | G06F 8/34 705/3 |

FOREIGN PATENT DOCUMENTS

| | | |
|---|---|---|
| CN | 118520157 A | 8/2024 |
| WO | 2022251587 A1 | 12/2022 |

OTHER PUBLICATIONS

Qiao Jin et al; Matching Patients to Clinical Trials with Large Language Models; Version 4. ArXiv. Preprint. NaN NaN [revised Apr. 27, 2024].

Bin Zhang et al; Harnessing artificial intelligence to improve clinical trial design; Communications Medicine vol. 3, Article No. 191 (2023).

* cited by examiner

*Primary Examiner* — Van H Oberly
(74) *Attorney, Agent, or Firm* — Caldwell Intellectual Property Law

(57) ABSTRACT

Apparatus for matching user data with third-party data structures include a processor and a memory communicatively connected to the processor, wherein the memory includes instructions configuring the processor to receive user data, create a query data structure as a function of the user data, query a data repository using the query data structure to identify a match, and generate a recommended course of action as a function of the match. The query data structure includes a query attribute and a first temporal attribute. The data repository includes a plurality of third-party data structures, wherein each third-party data structure includes a data feature and a second temporal attribute. Identifying the matches includes computing an overlap score and comparing the overlap score with a matching threshold.

18 Claims, 9 Drawing Sheets

$$\begin{bmatrix} Q_{11} & \cdots & Q_{1n} \\ \vdots & \ddots & \vdots \\ Q_{n1} & \cdots & Q_{nn} \end{bmatrix} \times \begin{bmatrix} W_{11} & \cdots & W_{1n} \\ \vdots & \ddots & \vdots \\ W_{n1} & \cdots & W_{nn} \end{bmatrix} \times \begin{bmatrix} F_{11} & \cdots & F_{1n} \\ \vdots & \ddots & \vdots \\ F_{n1} & \cdots & F_{nn} \end{bmatrix} \rightarrow \text{Overlap Score}$$

APPARATUS AND METHODS FOR MATCHING USER DATA WITH THIRD-PARTY DATA STRUCTURES

FIELD OF THE INVENTION

The present invention generally relates to the field of machine learning and digital health care. In particular, the present invention is directed to apparatus and methods for apparatus for matching user data with third-party data structures.

BACKGROUND

Matching complex user data with third-party data plays a crucial role in many decision-making processes but often proves to be challenging. One exemplary case of such data matching includes matching volunteers with clinical trial programs. Participating in clinical trials offers individuals an opportunity to contribute to medical advancements while potentially gaining access to new treatments. Clinical trials are not only critical for testing the safety and effectiveness of new treatments, but may also be particularly beneficial, sometimes even as a final resort, to patients suffering from challenging medical conditions that have limited treatment options. Such challenging medical conditions may include without limitation cancer, autoimmune diseases including lupus and/or multiple sclerosis, rare genetic disorders, chronic illnesses including diabetes and/or cardiovascular diseases, and/or neurodegenerative conditions including Alzheimer's and/or Parkinson's disease, among others. To participate in clinical trial programs, volunteers typically go through a screening process to determine eligibility based on the trial's criteria. However, participation in clinical trials can be challenging due to various factors. Such factors may include without limitation highly specific eligibility criteria, geographic limitations, demanding time commitment, potential side effects, uncertainty in outcomes, and poor accessibility to information including a limited awareness of available or soon-to-be available trials. As a result, some patients often struggle finding clinical trials that match their specific medical condition or treatment needs. Additionally, understanding the technical language and ensuring the trial is well-suited for a patient's stage of illness can make the search even more complex.

SUMMARY OF THE DISCLOSURE

In an aspect, an apparatus for matching user data with third-party data structures is described. The apparatus includes at least a processor and a memory communicatively connected to the at least a processor, wherein the memory contains instructions configuring the at least a processor to receive user data and create a query data structure as a function of the user data. The query data structure includes at least a query attribute and a first temporal attribute. The at least a processor is further configured to query a data repository using the query data structure to identify one or more matches. The data repository includes a plurality of third-party data structures. Each third-party data structure of the plurality of third-party data structures includes at least a data feature and a second temporal attribute associated. Identifying the one or more matches includes computing a first overlap as a function of the at least a query attribute and the at least a data feature, computing a second overlap as a function of the first temporal attribute and the second temporal attribute, computing an overlap score as a function of the first overlap, a first weight associated with the first overlap, the second overlap, and a second weight associated with the second overlap, and identifying the one or more matches by comparing the overlap score with one or more matching thresholds. The at least a processor is further configured to generate a recommended course of action as a function of the one or more matches.

In another aspect, a method for matching user data with third-party data structures is described. The method includes receiving, by at least a processor, user data and creating, by the at least a processor, a query data structure as a function of the user data. The query data structure includes at least a query attribute and a first temporal attribute. The method further includes querying, by the at least a processor, a data repository using the query data structure to identify one or more matches. The data repository includes a plurality of third-party data structures. Each third-party data structure of the plurality of third-party data structures includes at least a data feature and a second temporal attribute. Identifying the one or more matches includes computing a first overlap as a function of the at least a query attribute and the at least a data feature, computing a second overlap as a function of the first temporal attribute and the second temporal attribute, computing an overlap score as a function of the first overlap, a first weight associated with the first overlap, the second overlap, and a second weight associated with the second overlap, and identifying the one or more matches by comparing the overlap score with one or more matching thresholds. The method further includes generating, by the at least a processor, a recommended course of action as a function of the one or more matches.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a block diagram an exemplary workflow for computing an overlap score;

Figure 1:
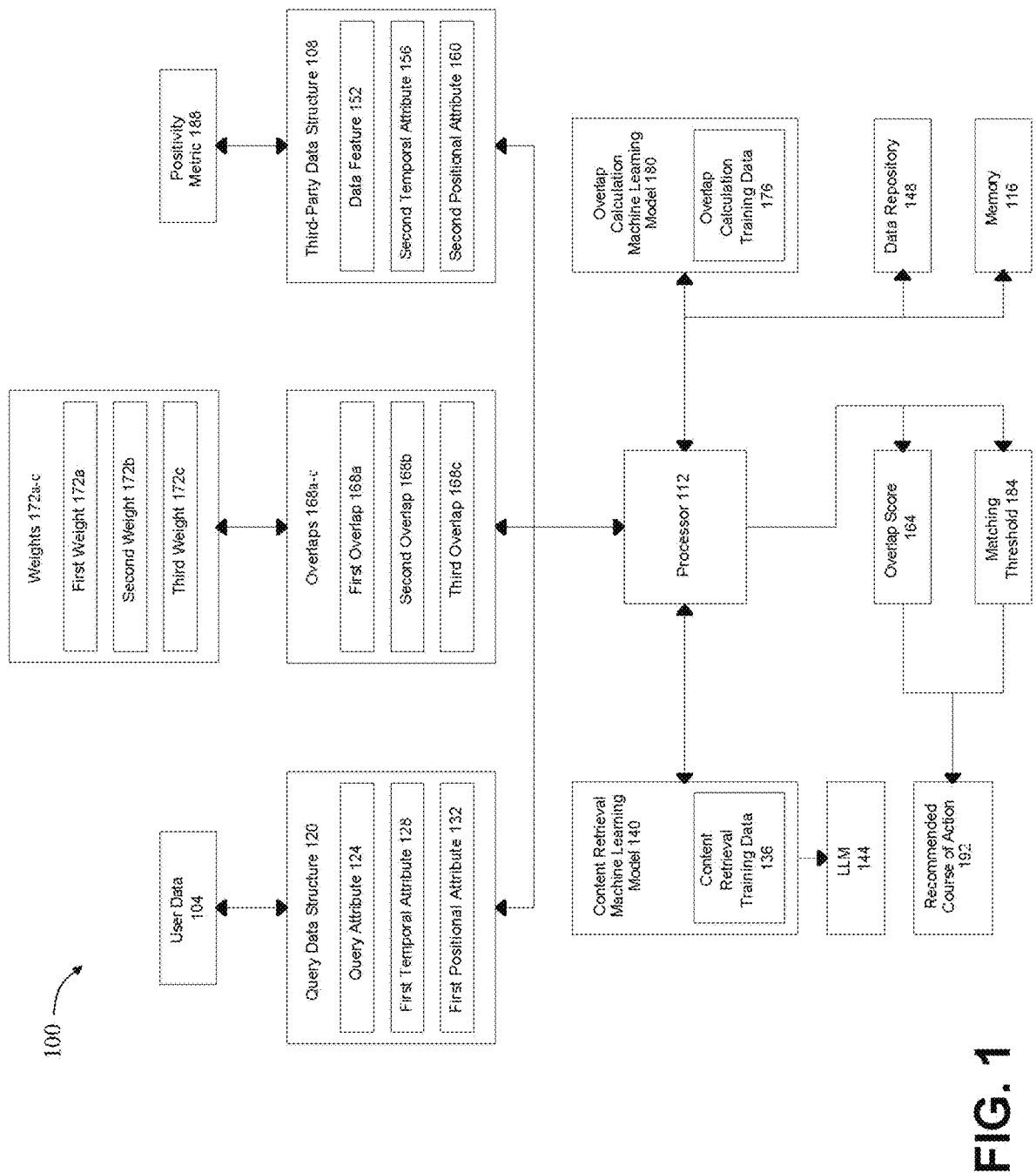
FIG. 1 is an exemplary block diagram of an apparatus that matches user data with third-party data structures.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for matching user data with third-party data structures. The apparatus includes at least a processor and a memory communicatively connected to the at least a processor, wherein the memory contains instructions configuring the at least a processor to receive user data and create a query data structure as a function of the user data. The query data structure includes at least a query attribute and a first temporal attribute. In one or more embodiments, the query data structure may further include a first positional attribute. In one or more embodiments, creating the query data structure may include receiving content retrieval training data including a plurality of exemplary query data structures as outputs correlated with a plurality of exemplary user data as inputs. The at least a processor may accordingly be configured to iteratively train a content retrieval machine-learning model using the content retrieval training data. The trained content retrieval machine-learning model may subsequently be used to create the query data structure. In some cases, the content retrieval machine-learning model may include a large language model (LLM) trained on a plurality of training examples and configured to extract text-based data. Training the LLM may include pretraining the LLM on a general set of training examples and retraining the LLM on a special set of training examples, wherein the general and the special set of training examples are subsets of the plurality of training examples.

The at least a processor is further configured to query a data repository using the query data structure to identify one or more matches. The data repository includes a plurality of third-party data structures. Each third-party data structure of the plurality of third-party data structures includes at least a data feature and a second temporal attribute. In one or more embodiments, each third-party data structure of the plurality of third-party data structures may further include a second positional attribute. In one or more embodiments, at least a third-party data structure of the plurality of third-party data structures may include one or more ongoing or scheduled clinical trial programs.

Identifying the one or more matches includes computing a first overlap as a function of the at least a query attribute and the at least a data feature. Identifying the one or more matches further includes computing a second overlap as a function of the first temporal attribute and the second temporal attribute. Identifying the one or more matches further includes computing an overlap score as a function of the first overlap, a first weight associated with the first overlap, the second overlap, and a second weight associated with the second overlap, and identifying the one or more matches by comparing the overlap score with one or more matching thresholds. In one or more embodiments, identifying the one or more matches may further include computing a third overlap as a function of the first positional attribute and the second positional attribute and computing the overlap score as a function of the third overlap and a third weight associated with the third overlap.

In one or more embodiments, computing the overlap score may include receiving overlap calculation training data including a plurality of exemplary overlap scores as outputs correlated with a plurality of exemplary query data structures as inputs. The at least a processor may be configured to iteratively train an overlap calculation machine-learning model using the overlap calculation training data by adjusting a plurality of weights. The trained overlap calculation machine-learning model may subsequently be used to calculate the overlap score. In one or more embodiments, each third-party data structure of the plurality of third-party data structures may be associated with a positivity metric. Accordingly, identifying the one or more matches may include filtering the plurality of third-party data structures as a function of the positivity metric and updating the identified one or more matches as a function of the filtered plurality of third-party data structures. In one or more embodiments, querying the data repository may include identifying one or more prior users associated with at least a third-party data structure of the plurality of third-party data structures.

The at least a processor is further configured to generate a recommended course of action as a function of the one or more matches. In one or more embodiments, the recommended course of action may include a treatment plan and/or a personalized medical solution. In one or more embodiments, the at least a processor is further configured to receive secondary user data. Such secondary user data may include user feedback explicitly provided by a user or status data automatically detected by the at least a processor. In some cases, such secondary user data may include real-time user data generated after an inception of a clinical trial program. The at least a processor may accordingly be configured to modify the query data structure as a function of the secondary user data and/or update the data repository as a function of the modified query data structure.

Aspects of the present disclosure may be used to accelerate complex data-matching processes in general. Aspects of the present disclosure may be used as an intelligent, adaptive digital healthcare platform. Aspects of the present disclosure may be used to facilitate a more accurate and efficient match between a user in need and a suitable clinical trial program. Exemplary embodiments illustrating aspects of the present disclosure are described below in the context of several specific examples.

Referring now to FIG. 1, an apparatus 100 for matching user data 104 with third-party data structures 108 is illustrated. For the purposes of this disclosure, a "user" is an individual in need of using or interacting with apparatus 100 or a custodian, agent, group, or organization representing the individual. In one or more embodiments, the user may include a patient. For the purposes of this disclosure, a "patient" is a human or any individual organism, on whom or on which a procedure, study, or otherwise experiment, may be conducted. As nonlimiting examples, a patient may include a human patient with symptoms of an autoimmune disease, an individual diagnosed with a neurodegenerative condition, a participant undergoing a clinical trial or willing to participate in a clinical trial, an individual with congenital heart disease, a heart transplant candidate, an individual receiving follow-up care after a surgery, a healthy volunteer, an individual with kidney failure, or the like. Additionally, and/or alternatively, a patient may include a pet such as without limitation a dog, a cat, a rabbit, a parrot, a fish, or the like. Additionally, or alternatively, a patient may include an animal model (i.e., an animal used to model certain medical conditions such as a laboratory rat). For the purposes of this disclosure, "user data" are data associated with a user. User data 104 may include any type of data directly or indirectly provided by a user, as recognized by a person of ordinary skill in the art, upon reviewing the entirety of this disclosure. In one or more embodiments, user data 104 may include textual data such as without limitation electronic notes, logs, or reports, online chat history, emails, text messages, and/or the like. In one or more embodiments, user data 104 may include audio data such as without limitation a recording of a conversation, a consulting session, an instruction, a therapeutic procedure, a telehealth session, a verbal consent by a patient, and/or the like. In one or more embodiments, user data 104 may include visual data such as without limitation a scanned image of a prescription or a doctor's note, an image of a prescription bottle, an image of a wound or infection, an X-ray image, a computed tomography (CT) scan, a magnetic resonance imaging (MRI) scan, an echocardiogram, an electrocardiogram, and/or the like. In one or more embodiments, user data 104 may include video data such as a video recording of a surgical procedure or a diagnostic evaluation. In one or more embodiments, user data 104 may include one or more digital files. For the purposes of this disclosure, a "digital file" is an electronic data unit stored in a computer-readable format. A digital file may be designed to encapsulate various types of information, including without limitation text, images, audio, video, and/or the like, as described above. A digital file may include without limitation a .doc file, a .docx file, a .ppt file, a .pptx file, a .pdf file, a .png file, a .jpeg file, a .html file, a .proto file, and/or the like. It is worth noting that such classification of data may sometimes be arbitrary, as certain types of data may be overlapping.

With continued reference to FIG. 1, in one or more embodiments, user data 104 may include or be associated with an electronic health record (EHR) pertaining to a user. For the purposes of this disclosure, an "electronic health record (EHR)" is a comprehensive collection of records relating to the health history, diagnosis, or condition of a patient, relating to treatment provided or proposed to be provided to the patient, or relating to additional factors that may impact the health of the patient. Elements within an EHR, once combined, may provide a detailed picture of patient's overall health. In one or more embodiments, an EHR may include demographic data and/or personal information of a patient. As nonlimiting examples, an EHR may include basic information about a patient such as name, age, gender, race, occupation, ethnicity, marital status, annual household income, socioeconomic status, insurance policy or insurance coverage, disability status, residential address, emergency contact, and/or the like. In one or more embodiments, an EHR may also include time-correlated data such as without limitation a patient's medical history. As nonlimiting examples, an EHR may include a detailed record of patient's past health conditions, medical procedures, hospitalizations, and illnesses such as surgeries, treatments, medications, allergies, and/or the like. In one or more embodiments, an EHR may include lifestyle information of a user. As nonlimiting examples, an EHR may include details about the patient's diet, daily calorie intake, exercise habits, smoking and alcohol consumption, use of recreational drugs, and/or other behaviors that could impact a user's health. In one or more embodiments, EHR may include patient's family history; for example, and without limitation, EHR may include a record of hereditary diseases. In one or more embodiments, an EHR may be retrieved from a database or a repository of similar nature as a database. Details regarding databases will be provided below in this disclosure.

With continued reference to FIG. 1, for the purposes of this disclosure, a "third-party data structure" is a data structure provided by or associated with one or more entities different from the user and apparatus 100. For the purposes of this disclosure, a "data structure" is a format of data organization, management, and storage that is usually chosen for efficient access to data. Data structures described herein may include any type of data structure recognized by a person of ordinary skill in the art upon reviewing the entirety of this disclosure, such as without limitation, stack, queue, array, list, or tree. In some cases, a third-party data structure may include a third-party event. For the purposes of this disclosure, an "event" is an organized collection of data or activities. In one or more embodiments, an event may include a clinical trial program associated with one or more drugs or therapies under development, such as without limitation a Phase I, a Phase II, a Phase III, or a Phase IV clinical trial. Such clinical trial program may be either ongoing or scheduled for a future date. For the purposes of this disclosure, a "clinical trial" is a structured research process, usually involving human participants, that is conducted to evaluate the safety, efficacy, and potential benefits of a medical intervention. Such medical intervention may include without limitation a drug or therapy. Phase I of a clinical trial tests the safety and dosage of the medical intervention in a small group to determine side effects. Phase II of a clinical trial assesses the effectiveness of a medical intervention in a larger group while further monitoring its safety. Phase III expands the study population to confirm the efficacy of a medical intervention, monitor its adverse reactions, and compare it with standard treatments. Phase IV sometimes occurs post-approval to track the long-term safety and benefits of a medical intervention in broader populations. For the purposes of this disclosure, an "entity" is a natural person, a group of individuals, a corporate or organization, a department or division within a corporate or organization, or otherwise any subject or party responsible for or otherwise associated with a third-party data structure 108. In one or more embodiments, an entity may include a pharmaceutical company, a research institution, a division within or a representative of a pharmaceutical company and/or a research institution, or an individual researcher or inventor that is expected to sponsor, lead, monitor, participate in, or otherwise be held partially or fully responsible for a clinical trial program.

With continued reference to FIG. 1, apparatus 100 includes at least a processor 112. In one or more embodiments, at least a processor 112 may include or be included in a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially, or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1, apparatus 100 includes a memory 116 communicatively connected to at least a processor 112, wherein the memory 116 contains instructions configuring the at least a processor 112 to perform any processing steps described herein. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1, computing device may perform determinations, classification, and/or analysis steps, methods, processes, or the like as described in this disclosure using machine-learning processes. For the purposes of this disclosure, a "machine-learning process" is a process that automatedly uses a body of data known as "training data" and/or a "training set" to generate an algorithm that will be performed by a processor module to produce outputs given data provided as inputs. This is in contrast to a non-machine-learning software program where the commands to be executed are determined in advance by a user and written in a programming language. A machine-learning process may utilize supervised, unsupervised, lazy-learning processes and/or neural networks. More details regarding computing devices and machine-learning processes will be provided below.

With continued reference to FIG. 1, in one or more embodiments, one or more machine-learning models may be used to perform certain function or functions of apparatus 100, such as without limitation population of a query data structure and/or calculation of an overlap score, as described below. Processor 112 may use a machine-learning module to implement one or more algorithms as described herein or generate one or more machine-learning models, such as feature extraction model, as described below. However, machine-learning module is exemplary and may not be necessary to generate one or more machine-learning models and perform any machine learning described herein. In one or more embodiments, one or more machine-learning models may be generated using training data. Training data may include inputs and corresponding predetermined outputs so that machine-learning model may use correlations between the provided exemplary inputs and outputs to develop an algorithm and/or relationship that then allows the machine-learning model to determine its own outputs for inputs. Training data may contain correlations that a machine-learning process may use to model relationships between two or more categories of data elements. Exemplary inputs and outputs may be retrieved from a database, selected from one or more EHRs, or be provided by a user. In one or more embodiments, machine-learning module may obtain training data by querying a communicatively connected database that includes past inputs and outputs. Training data may include inputs from various types of databases, resources, and/or user inputs and outputs correlated to each of those inputs, so that machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In one or more embodiments, training data may include previous outputs such that one or more machine-learning models may iteratively produce outputs.

With continued reference to FIG. 1, at least a processor 112 is configured to receive user data 104, consistent with details described above. In one or more embodiments, user data 104 may be provided via direct user input, such as without limitation using a user interface. In some cases, a user may provide user data 104 by completing one or more onboarding surveys or questionnaires or uploading one or more digital files. In one or more embodiments, receiving user data 104 may include generating one or more prompts in an interactive digital environment and receiving user data 104 from a user in response to the one or more prompts. For the purposes of this disclosure, a "prompt" is a directive or input request generated by a software application or operating system, instructing the user to provide specific information or perform an action. As a nonlimiting example, a prompt may refer to an interactive query displayed on a user interface, awaiting a user input or response to proceed with a particular process or task. Such interaction may occur in various forms, such as text prompts in command-line interfaces, dialogue boxes in graphical user interfaces, or spoken prompts in voice-controlled systems, among others. A prompt may be generated using any suitable format as recognized by a person of ordinary skill in the art. As a nonlimiting example, a prompt may be generated as onboarding questions or questionnaires, surveys, and/or the like. As a further nonlimiting example, a prompt may be synthesized using a machine-learning model, such as without limitation a large language model (LLM). Additional details regarding LLMs will be provided below in this disclosure.

With continued reference to FIG. 1, in some cases, a prompt may be implemented as an audio prompt using a speech synthesis algorithm. For the purposes of this disclosure, a "speech synthesis algorithm" is a machine learning algorithm configured to synthesize language text into speech, capturing nuances such as without limitation dialects, accents, pausing, and intonations. In some cases, a speech synthesis algorithm may be implemented as a speech synthesis machine learning model, consistent with details described elsewhere in this disclosure. Specifically, training such a speech synthesis machine learning model may include receiving speech synthesis training data including a plurality of training texts as inputs and a plurality of training audio data as outputs and training the speech synthesis machine learning model by correlating the plurality of training texts with the plurality of training audio data. Accordingly, at least a processor 112 may be configured to synthesize an audio prompt using the trained speech synthesis machine learning model. Implementation of this machine learning model may be consistent with any type of machine learning model or algorithm described in this disclosure. In one or more embodiments, speech synthesis training data may include data specifically synthesized for training purposes using one or more generative models, as described in this disclosure. In one or more embodiments, one or more datasets from previous sessions may be incorporated into speech synthesis training data upon validation. In one or more embodiments, speech synthesis training data may be retrieved from one or more databases and/or other repositories of similar nature or be supplied as one or more inputs from one or more users. In one or more embodiments, at least a portion of speech synthesis training data may be added, deleted, replaced, or otherwise updated as a function of one or more inputs from one or more users. A person of ordinary skill in the art, upon reviewing the entirety of this disclosure, will be able to recognize suitable means to implement a speech synthesis algorithm in apparatus 100. Additional details will be provided below in this disclosure.

With continued reference to FIG. 1, for the purposes of this disclosure, a "digital environment" is an integrated communications environment where digital devices communicate and manage data and interactions within the digital environment. Digital device may include any computing device as described in this disclosure. Additionally, any processing step described in this disclosure may be performed in digital environment. For example, digital environment may be one of a computer system, computer network, and the like. In an exemplary embodiment, the digital environment may include a plurality of remote devices, as described in detail below in this disclosure. In some embodiments, digital environment may also include any electronically based asset associated with the digital environment. For example, electronically based digital assets may be computer programs, data, data stores, and the like, but are not limited to such examples. Digital environment may be connected to a processor by a network. Digital environment may employ any type of network architecture. For example, digital environment may employ a peer-to-peer (P2P) architecture where each computing device in a computing network is connected with every computing device in the network and every computing device acts as a server for the data stored in the computing device. In a further exemplary embodiment, digital environment may also employ a client server architecture where a computing device is implemented as a central computing device (e.g., server) that is connected to each client computing device and communication is routed through the central computing device. However, network architecture is not limited thereto. Further, any network topology may be used. For example, digital environment may employ a mesh topology where a computing device is connected to one or multiple other computing devices using point-to-point connections. However, network topology is not limited thereto. A person of ordinary skill in the art will be able to recognize the various network architectures that may be employed by digital environment upon reviewing the entirety of this disclosure.

With continued reference to FIG. 1, in one or more embodiments, apparatus 100 may implement a virtual avatar in order to perform one or more aspects of its functions. For the purposes of this disclosure, a "virtual avatar" is a digitally constructed representation of a user or character designed to interact within a virtual or digital environment. A virtual avatar may refer to a graphical, three-dimensional model or animated figure that may be configured, customized, and/or controlled by a user to represent their presence in virtual spaces such as virtual reality (VR) or augmented reality (AR) environments, online games, and social media platforms, among others. A virtual avatar may enable or facilitate user interaction, communication, and engagement within digital interfaces and immersive experiences. Specifically, in some cases, a virtual avatar may be configured as a virtual agent that monitors how a user interacts with apparatus 100 and proceeds with an informational, educational, or training program.

With continued reference to FIG. 1, details described herein may be consistent with any detail disclosed in U.S. Pat. No. 12,073,930, patented on Aug. 27, 2024, entitled "APPARATUS AND A METHOD FOR GENERATING A USER REPORT", U.S. patent application Ser. No. 18/426,617, filed on Jan. 30, 2024, entitled "APPARATUS AND METHOD FOR GENERATING A TEXT OUTPUT", and U.S. patent application Ser. No. 18/762,268, filed on Jul. 2, 2024, entitled "SYSTEM AND METHODS FOR DELIVERING CONTEXTUAL RESPONSES THROUGH DYNAMIC INTEGRATIONS OF DIGITAL INFORMATION REPOSITORIES WITH INQUIRIES", the entirety of each of which is incorporated herein by reference.

With continued reference to FIG. 1, at least a processor 112 is configured to create a query data structure 120 as a function of user data 104. For the purposes of this disclosure, a "query data structure" is a data structure that can be used as query to retrieve information and/or initiate subsequent processing steps. Query data structure 120 includes at least a query attribute 124. For the purposes of this disclosure, a "query attribute" is a data element containing information for which a user is aiming to find a solution using apparatus 100. In one or more embodiments, query attribute 124 may include or specify a medical condition associated with a user, such as without limitation a case of cancer, a case of an autoimmune disease (e.g., lupus, multiple sclerosis and/or the like), a case of a genetic disorder, a case of chronic illnesses (e.g., diabetes, cardiovascular diseases, and/or the like), and/or a case of a neurodegenerative condition (e.g., Alzheimer's disease, Parkinson's disease, and/or the like). Additionally, query attribute 124 may include one or more specific attributes of such medical conditions, such as the time of inception, stage of the medical condition (e.g., Stage Zero, I, II, III, or IV of cancer), record of relapse(s) and remission(s), average/peak level of severity, among others. Apparatus 100 may accordingly identify suitable clinical trial programs for treating or mitigating such medical condition, as described in detail below in this disclosure.

With continued reference to FIG. 1, for the purposes of this disclosure, query data structure 120 includes a first temporal attribute 128. For the purposes of this disclosure, a "temporal attribute" is a time-related data element specified by its starting time, ending time, and a span in between. In one or more embodiments, a first temporal attribute 128 may include a required or preferred starting time, ending time, and/or duration of a clinical trial program that a user is willing to consider for participation. In some cases, a first temporal attribute 128 may further include a level of leniency. Such level of leniency may include without limitation how flexible a user may be regarding the starting time, ending time, and/or duration of a clinical trial program. Additional details will be provided in this disclosure.

With continued reference to FIG. 1, in one or more embodiments, query data structure 120 may further include a first positional attribute 132. For the purposes of this disclosure, a "positional attribute" is a data element pertaining to the location of a user, party, or entity. In one or more embodiments, a positional attribute may include a location pertaining to a user (i.e., a first positional attribute 132), such as without limitation a residential address of a user or a location at which a user is being treated or hospitalized, among others. In one or more embodiments, a positional attribute may include the location or locations of one or more facilities associated with third-party data structure 108 (i.e., a second positional attribute, as described below), such as without limitation the location or locations where a clinical trial program is implemented. In one or more embodiments, a positional attribute may include a combination of longitude and latitude, an address, a street name, a city/county/state name, a zip code, and/or the like. First positional attribute 132 may be used as a point of reference by apparatus 100 in its subsequent processing steps, as described in further detail below in this disclosure.

With continued reference to FIG. 1, in one or more embodiments, creating query data structure 120 may involve using a machine-learning model. Specifically, creating query data structure 120 may include receiving content retrieval training data 136 including a plurality of exemplary query data structures as outputs correlated with a plurality of exemplary user data as inputs. At least a processor 112 may accordingly be configured to iteratively train a content retrieval machine-learning model 140 using content retrieval training data 136. Trained content retrieval machine-learning model 140 may subsequently be used to create query data structure 120. Implementation of this machine learning model may be consistent with any type of machine learning model or algorithm described in this disclosure. In one or more embodiments, content retrieval training data may include data specifically synthesized for training purposes using one or more generative models, as described in this disclosure. In one or more embodiments, one or more datasets from previous queries may be incorporated into content retrieval training data 136 upon validation. In one or more embodiments, content retrieval training data 136 may be retrieved from one or more databases and/or other repositories of similar nature or be supplied as one or more inputs from one or more users. In one or more embodiments, at least a portion of content retrieval training data 136 may be added, deleted, replaced, or otherwise updated as a function of one or more inputs from one or more users. A person of ordinary skill in the art, upon reviewing the entirety of this disclosure, will be able to recognize suitable means to implement content retrieval machine-learning model 140 in apparatus 100.

With continued reference to FIG. 1, in some cases, content retrieval machine-learning model 140 may include a large language model (LLM) 144 trained on a plurality of training examples and configured to extract text-based data. In some cases, an LLM 144 may be configured to extract textual information from unstructured user data 104. In some cases, an LLM 144 may be configured to preprocess unstructured data, such as without limitation standardizing and verifying information therein. As a nonlimiting example, an LLM 144 may be configured to first analyze an audio input to generate a transcript or the like, and then access the textural information therein for additional downstream processing steps. Training LLM 144 may include pretraining the LLM 144 on a general set of training examples and retraining the LLM 144 on a special set of training examples, wherein the general and the special set of training examples are subsets of the plurality of training examples. For the purposes of this disclosure, a "large language model" is a deep learning data structure that can recognize, summarize, translate, predict and/or generate text and other content based on knowledge gained from massive datasets. LLMs may be trained on large sets of data. Training examples may be drawn from diverse sets of data such as, as nonlimiting examples, scientific journal articles, medical report documents, EHRs, entity documents, business documents, inventory documentation, emails, user communications, advertising documents, newspaper articles, and the like. In some embodiments, training examples of an LLM may include information from one or more public or private databases or data repositories similar thereto. As a nonlimiting example, training examples may include databases associated with an entity. In some embodiments, training sets may include portions of documents associated with the electronic records correlated to examples of outputs. In one or more embodiments, LLM may include one or more architectures based on capability requirements of the LLM. Exemplary architectures may include, without limitation, Generative Pretrained Transformer (GPT), Bidirectional Encoder Representations from Transformers (BERT), Text-To-Text Transfer Transformer (T5), and the like. Architecture choice may depend on a needed capability, such as without limitation generative, contextual, or other specific capabilities, among others.

With continued reference to FIG. 1, in one or more embodiments, LLM may be generally trained. For the purposes of this disclosure, a "generally trained" LLM is a LLM that is trained on a general training set comprising a variety of subject matters, data sets, and fields. In one or more embodiments, LLM may be initially generally trained. Additionally, or alternatively, LLM may be specifically trained. For the purposes of this disclosure, a "specifically trained" LLM is a LLM that is trained on a specific training set, wherein the specific training set includes data including specific correlations for the LLM to learn. As a nonlimiting example, LLM may be generally trained on a general training set, then specifically trained on a specific training set. In one or more embodiments, generally training LLM may be performed using unsupervised machine-learning process. In one or more embodiments, specific training of LLM may be performed using supervised machine-learning process. As a nonlimiting example, specific training set may include information from a database. As a nonlimiting example, specific training set may include text related to the users such as user specific data for electronic records correlated to examples of outputs. In one or more embodiments, training one or more machine-learning models may include setting the parameters of the one or more models (weights and biases) either randomly or using a pretrained model. Generally training one or more machine-learning models on a large corpus of text data can provide a starting point for fine-tuning on a specific task. A model such as LLM may learn by adjusting its parameters during the training process to minimize a defined loss function, which measures the difference between predicted outputs and ground truth. Once model has been generally trained, the model may then be specifically trained to fine-tune the pretrained model on task-specific data to adapt it to the target task. Fine-tuning may involve training model with task-specific training data, adjusting the model's weights to optimize performance for the particular task. In some cases, this may include optimizing model's performance by fine-tuning hyperparameters such as learning rate, batch size, and regularization. Hyperparameter tuning may help in achieving the best performance and convergence during training. In one or more embodiments, fine-tuning pretrained model such as LLM may include fine-tuning the pretrained model using Low-Rank Adaptation (LoRA). For the purposes of this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in one or more embodiments, LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. LLM may include a text prediction-based algorithm configured to receive an article and apply a probability distribution to the words already typed in a sentence to work out the most likely word to come next in augmented articles. For example, if some words that have already been typed are "electronic health", then it may be highly likely that the word "record" will come next. LLM may output such predictions by ranking words by likelihood or a prompt parameter. For the example given above, LLM may score "record" as the most likely, "records" as the next most likely, "profile" or "profiles" next, and the like. LLM may include an encoder component and a decoder component.

With continued reference to FIG. 1, LLM may include a transformer architecture. In some embodiments, encoder component of LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. For the purposes of this disclosure, "positional encoding" is a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM and/or transformer architecture may include an attention mechanism. For the purposes of this disclosure, an "attention mechanism" is a part of a neural network architecture that enables a system to dynamically quantify relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decoder model encodes an input sequence to one fixed-length vector from which the output is decoded at each time step. This issue may be seen as a problem when decoding long sequences because it may make it difficult for the neural network to cope with long sentences, such as those that are longer than the sentences in the training corpus. Applying attention mechanism, LLM may predict next word by searching for a set of positions in a source sentence where the most relevant information is concentrated. LLM may then predict next word based on context vectors associated with these source positions and all the previously generated target words, such as textual data of a dictionary correlated to a prompt in a training data set. For the purposes of this disclosure, "context vectors" are fixed-length vector representations useful for document retrieval and word sense disambiguation.

With continued reference to FIG. 1, attention mechanism may include, without limitation, generalized attention, self-attention, multi-head attention, additive attention, global attention, and the like. In generalized attention, when a sequence of words or an image is fed to LLM, it may verify each element of input sequence and compare it against the output sequence. Each iteration may involve the mechanism's encoder capturing input sequence and comparing it with each element of the decoder's sequence. From the comparison scores, attention mechanism may then select the words or parts of image that it needs to pay attention to. In self-attention, LLM may pick up particular parts at different positions in input sequence and over time compute an initial composition of output sequence. In multi-head attention, LLM may include a transformer model of an attention mechanism. Attention mechanisms, as described above, may provide context for any position in input sequence. For example, if the input data is a natural-language sentence, the transformer does not have to process one word at a time. In multi-head attention, computations by LLM may be repeated over several iterations, and each computation may form parallel layers known as attention heads. Each separate head may independently pass input sequence and corresponding output sequence element through separate head. A final attention score may be produced by combining attention scores at each head so that every nuance of input sequence is taken into consideration. In additive attention (Bahdanau attention mechanism), LLM may make use of attention alignment scores based on a number of factors. Alignment scores may be calculated at different points in neural network, and/or at different stages represented by discrete neural networks. Source or input sequence words are correlated with target or output sequence words but not to an exact degree. This correlation may take into account all hidden states and the final alignment score is the summation of a matrix of alignment scores. In global attention (Luong mechanism), in situations where neural machine translations are required, LLM may either attend to all source words or predict the target sentence, thereby attending to a smaller subset of words.

With continued reference to FIG. 1, multi-headed attention in encoder may apply a specific attention mechanism called self-attention. Self-attention allows models such as LLM or components thereof to associate each word in input, to other words. As a nonlimiting example, LLM may learn to associate the word "you", with "how" and "are". It's also possible that LLM learns that words structured in this pattern are typically a question and to respond appropriately. In one or more embodiments, to achieve self-attention, input may be fed into three distinct and fully connected neural network layers to create query, key, and value vectors. Query, key, and value vectors may be fed through a linear layer; then, the query and key vectors may be multiplied using dot product matrix multiplication in order to produce a score matrix. Score matrix may determine the amount of focus for a word that should be put on other words (thus, each word may be a score that corresponds to other words in the time-step). The values in score matrix may be scaled down. As a nonlimiting example, score matrix may be divided by the square root of the dimension of the query and key vectors. In one or more embodiments, a softmax of the scaled scores in score matrix may be taken. The output of this softmax function may be called attention weights. Attention weights may be multiplied by your value vector to obtain an output vector, wherein the output vector may then be fed through a final linear layer.

With continued reference to FIG. 1, in order to use self-attention in a multi-headed attention computation, query, key, and value may be split into N vectors before applying self-attention. Each self-attention process may be called a "head". Each head may produce an output vector and each output vector from each head may be concatenated into a single vector. This single vector may then be fed through final linear layer discussed above. In theory, each head can learn something different from input, therefore giving the encoder model more representation power.

With continued reference to FIG. 1, encoder of transformer may include a residual connection. Residual connection may include adding the output from multi-headed attention to the positional input embedding. In one or more embodiments, an output from residual connection may go through a layer normalization. In one or more embodiments, a normalized residual output may be projected through a pointwise feed-forward network for further processing. Pointwise feed-forward network may include a couple of linear layers with a ReLU activation in between. Output may then be added to an input of the pointwise feed-forward network and further normalized.

With continued reference to FIG. 1, transformer architecture may include a decoder. Decoder may include a multi-headed attention layer, a pointwise feed-forward layer, one or more residual connections, and layer normalization (particularly after each sub-layer), as discussed in more detail above. In one or more embodiments, decoder may include two multi-headed attention layers. In one or more embodiments, decoder may be autoregressive. For the purposes of this disclosure, "autoregressive" means that the decoder takes in a list of previous outputs as inputs along with encoder outputs containing attention information from the input.

With continued reference to FIG. 1, in one or more embodiments, input to decoder may go through an embedding layer and positional encoding layer to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a nonlimiting example, when computing attention scores on the word "am", decoder should not have access to the word "fine" in "I am fine", because that word is a future word that was generated after. The word "am" should only have access to itself and the words before it. In one or more embodiments, this may be accomplished by implementing a look-ahead mask. Look ahead mask is a matrix of the same dimensions as a scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when a softmax of this matrix is taken, negative infinities will be zeroed out; this leaves zero attention scores for "future tokens."

With continued reference to FIG. 1, second multi-headed attention layer may use encoder outputs as queries and keys and outputs from the first multi-headed attention layer as values. This process matches encoder's input to the decoder's input, allowing the decoder to decide which encoder input is relevant to put a focus on. An output from second multi-headed attention layer may be fed through a pointwise feedforward layer for further processing.

With continued reference to FIG. 1, an output of the pointwise feedforward layer may be fed through a final linear layer. This final linear layer may act as a classifier. This classifier may be as big as the number of classes that you have. For example, if you have 10,000 classes for 10,000 words, output of that classifier will be of size 10,000. Output of this classifier may be fed into a softmax layer which may serve to produce probability scores between zero and one. An index may be taken of the highest probability score in order to determine a predicted word.

With continued reference to FIG. 1, decoder may take this output and add it to decoder inputs. Decoder may continue decoding until a token is predicted. Decoder may stop decoding once it predicts an end token.

With continued reference to FIG. 1, in one or more embodiments, decoder may be stacked N layers high, with each layer taking in inputs from encoder and layers before it. Stacking layers may allow LLM to learn to extract and focus on different combinations of attention from its attention heads.

With continued reference to FIG. 1, LLM may receive an input. Input may include a string of one or more characters. Inputs may additionally include unstructured data. For example, input may include one or more words, a sentence, a paragraph, a thought, a query, and the like. For the purposes of this disclosure, a "query" is a string of characters that poses a question. In one or more embodiments, input may be received from a user device. User device may be any computing device that is used by a user. As nonlimiting examples, user device may include desktops, laptops, smartphones, tablets, and the like. In one or more embodiments, input may include any set of data associated with training and/or using LLM. As a nonlimiting example, input may be a prompt such as "what abnormalities are present in the attached medical image?"

With continued reference to FIG. 1, LLM may generate at least one annotation as output. At least one annotation may be any annotation as described herein. In one or more embodiments, LLM may include multiple sets of transformer architecture as described above. Output may include a textual output. For the purposes of this disclosure, "textual output" is an output comprising a string of one or more characters. Textual output may include, for example, a plurality of annotations for unstructured data. In one or more embodiments, textual output May include a phrase or sentence identifying the status of a user query. In one or more embodiments, textual output may include a sentence or plurality of sentences describing a response to user query. As a nonlimiting example, this may include restrictions, timing, advice, dangers, benefits, and the like.

With continued reference to FIG. 1, apparatus 100 may include or be communicatively connected to a data repository 148. For the purposes of this disclosure, a "data repository" is a centralized storage location where large volumes of data are collected, managed, and/or maintained for future retrieval, analysis, or distribution. A data repository can be a physical or virtual location used to store structured, semi-structured, or unstructured data. Data repositories are commonly used in scientific research, healthcare, business, and IT for securely storing data from various sources, making it easily accessible for analysis, reporting, or sharing. Nonlimiting examples of data repositories may include databases, data warehouses, and/or cloud storage solutions, among others. For the purposes of this disclosure, a "database" is an organized collection of data or a type of data store based on the use of a database management system (DBMS), the software that interacts with end users, applications, and the database itself to capture and analyze the data. Database may be implemented, without limitation, as a relational database, a key-value retrieval database such as a NoSQL database, or any other format or structure for use as database that a person of ordinary skill in the art would recognize as suitable upon review of the entirety of this disclosure. Database may alternatively, or additionally, be implemented using a distributed data storage protocol and/or data structure, such as a distributed hash table or the like. Database may include a plurality of data entries and/or records as described in this disclosure. Data entries in database may be flagged with or linked to one or more additional elements of information, which may be reflected in data entry cells and/or in linked tables such as tables related by one or more indices in database or another relational database. A person of ordinary skill in the art, upon reviewing the entirety of this disclosure, will be aware of various ways in which data entries in database may store, retrieve, organize, and/or reflect data and/or records as used herein, as well as categories and/or populations of data consistently with this disclosure.

With continued reference to FIG. 1, in some cases, at least a processor 112 may be configured to query a database by searching within the database for a match. As a nonlimiting example, when a database includes a SQL database, processor 112 may be configured to submit one or more SQL queries to interact with the database. To retrieve data, a "SELECT" statement may be used to specify one or more columns, rows, table names, and/or the like, and optional conditions may be applied using WHERE clauses. In some cases, a DBMS may use indexes, if available, to quickly locate relevant rows and columns, ensuring accurate and efficient data retrieval. Once SQL queries are executed using a DBMS interface or code, results may be returned for further steps.

With continued reference to FIG. 1, at least a processor 112 is further configured to query data repository 148 using query data structure 120 to identify one or more matches, consistent with details described above. Data repository 148 includes a plurality of third-party data structures 108, consistent with details described above. In one or more embodiments, data repository 148 may include one or more proprietary databases containing deidentified user data. Each third-party data structure 108 of the plurality of third-party data structures 108 includes at least a data feature 152. For the purposes of this disclosure, an "data feature" is a descriptor pertaining to one or more aspects of the nature of a data structure. In one or more embodiments, for a clinical trial program, data feature 152 may include the type of disease, medical condition, or symptoms that a drug or therapy is intended to treat or mitigate. Additionally and/or alternatively, in one or more embodiments, data feature 152 may outline certain restrictions regarding the eligibility of volunteers participating in a clinical trial, such as without limitation age, gender, race/ethnicity, body mass index (BMI), blood pressure, blood glucose level, body fat percentage, low-density lipoprotein (LDL) cholesterol level, high-density lipoprotein (HDL) cholesterol level, total cholesterol level, triglyceride level, subtype and/or severity of certain medical condition or conditions, expected level of commitment (e.g., the number or frequency of visits throughout the clinical trial), and/or one or more restrictions regarding diets, consumption of tobacco/alcohol/recreational drugs, medications, etc.

With continued reference to FIG. 1, third-party data structure 108 may include a second temporal attribute 156, consistent with details described above pertaining to first temporal attribute 128. In one or more embodiments, for the case of an ongoing or scheduled clinical trial program, second temporal attribute 156 may include or specify a starting date, ending date, and span of the clinical trial program. Similarly, in some cases, third-party data structure 108 may include a second positional attribute 160, consistent with details described above pertaining to first positional attribute. In one or more embodiments, for the case of an ongoing or scheduled clinical trial program, second positional attribute 160 may include or specify one or more locations where the clinical trial program may be conducted. Second temporal attribute 156 and/or second positional attribute 160 will be compared with first temporal attribute 128 and first positional attribute 132, respectively, as described above, in order to identify one or more matching third-party data structures 108. Additional details will be provided below in this disclosure.

With continued reference to FIG. 1, identifying the one or more matches includes computing an overlap score 164 between query data structure 120 and each third-party data structure 108 of the plurality of third-party data structures 108 and identifying the one or more matches as a function of the overlap score 164. For the purposes of this disclosure, an "overlap score" is a numerical indication that describes how two data structures align with each other. A higher overlap score may indicate a more compatible pair of data structures, whereas a lower overlap score may include a less compatible pair of data structures instead. Overlap score 164 may be expressed using any suitable numerical scale, as recognized by a person of ordinary skill in the art, upon reviewing the entirety of this disclosure. As nonlimiting examples, overlap score 164 may be expressed on a scale of 5, 10, 100 (e.g., as a percentage), or the like. Computation of overlap score 164 may require weighing and aggregating multiple overlaps between multiple pairs of data elements. Additional details will be provided below regarding how overlap score 164 may be computed.

With continued reference to FIG. 1, computing overlap score 164 includes computing a first overlap 168*a* as a function of at least a query attribute 124 and at least a data feature 152. For the purposes of this disclosure, an "overlap" is a metric describing how closely two data elements are aligned with one other. In some cases, first overlap 168*a* may be described using a binary metric, such as 0 vs. 1. As a nonlimiting example, if a query attribute 124 specifies that a user is seeking a clinical trial program for treatment of Type I diabetes, but a data feature 152 of third-party data structure 108 indicates that a clinical trial is targeted at evaluating a new generation of antidepressants, first overlap 168*a* may be assigned as zero, which indicates a poor match. As another nonlimiting example, if a query attribute 124 specifies that a user is 65 years old, and a data feature 152 of third-party data structure 108 indicates that a clinical trial is recruiting volunteers exclusively between the age of 50 and 70 years old, first overlap 168*a* may accordingly be assigned as "1", which indicates a satisfactory match. In some other cases, first overlap 168*a* may be described using a metric on a continuous scale. Accordingly, such first overlap 168*a* may be specified and/or categorized, for example and without limitation, as a satisfactory match (0.8-1), an upper-medium-level match (0.6-0.8), a medium-level match (0.4-0.6), a lower-medium-level match (0.2-0.4), and a poor match (0-0.1). As a nonlimiting example, if a query attribute 124 specifies that a user is diagnosed with breast cancer, and a data feature 152 of third-party data structure 108 indicates that a clinical trial is recruiting volunteers that primarily include patients diagnosed with lung cancer, first overlap 168*a* may accordingly be assigned as "0.5", which indicates a medium-level match. As a nonlimiting example, if a query attribute 124 specifies that a user is diagnosed with Stage II lung cancer, and a data feature 152 of third-party data structure 108 indicates that a clinical trial is recruiting volunteers that primarily include patients diagnosed with Stage III lung cancer, first overlap 168*a* may accordingly be assigned as "0.8", which indicates an upper-medium-level match. A continuous scale may be particularly useful when a clinical trial program targets a family of related diseases or conditions. In some cases, a new drug may have one primary target condition and one or more secondary target conditions, where the drug is still likely to be effective. As nonlimiting examples, some types of cancer may be treated using similar medications; while specific treatments are tailored to the type and stage of cancer, some therapies overlap across these types. Breast cancer, prostate cancer, and lung cancer may all respond to hormone therapy or targeted therapies. Similarly, colorectal cancer and stomach cancer may sometimes be treated with chemotherapy drugs including fluoropyrimidines or the like. Lymphomas and leukemias may also be treated using immune checkpoint inhibitors or other immunotherapies that target immune system pathways. As further nonlimiting examples, several autoimmune diseases may be treated using similar medications, particularly immunosuppressants and biologics that target the immune system. Rheumatoid arthritis, lupus, and psoriatic arthritis may be treated with medications including methotrexate, which suppresses immune activity. Inflammatory bowel diseases such as Crohn's disease and ulcerative colitis can may respond to similar treatments like TNF inhibitors (e.g., infliximab or adalimumab, among others). These medications may help reduce inflammation by targeting the immune system's overactive components across different conditions.

With continued reference to FIG. 1, computing overlap score 164 further includes computing a second overlap 168*b* as a function of first temporal attribute 128 and second temporal attribute 156. For the case of a clinical trial program, second overlap 168*b* may be used to gauge how a user's timeline aligns with the timeline of a clinical trial schedule. Second overlap 168*b* may be described or represented using any suitable means described above pertaining to first overlap 168*a*, such as without limitation using a binary or a continuous scale. As a nonlimiting example, if a first temporal attribute 128 specifies that a user is seeking a clinical trial program that starts in January 2025, but a second temporal attribute 156 of third-party data structure 108 indicates that a clinical trial is scheduled for December 2025, second overlap 168*b* may be assigned as zero, which indicates a poor match. As another nonlimiting example, if a first temporal attribute 128 specifies that a user is seeking a clinical trial program that starts in the second quarter of 2025, and a second temporal attribute 156 of third-party data structure 108 indicates that a clinical trial is scheduled for May 2025, second overlap 168*b* may be assigned as 1, which indicates a satisfactory match. As another nonlimiting example, if a first temporal attribute 128 specifies that a user is seeking a clinical trial program that preferably starts in January 2025, and a second temporal attribute 156 of third-party data structure 108 indicates that a clinical trial is recruiting volunteers for participation preferably between March 2025 and August 2025, second overlap 168*b* may be assigned as 0.5, which indicates a medium-level match.

With continued reference to FIG. 1, in one or more embodiments, computing overlap score 164 may further include computing a third overlap 168*c* as a function of first positional attribute 132 and second positional attribute 160. For the case of a clinical trial program, third overlap 168*b* may be used to gauge how compatible a user's location is with respect to the one or more available locations of a clinical trial. In some cases, a user may be bound by a certain geographical area, such as without limitation a state border, due to restrictions imposed by an insurance policy or the like. Accordingly, third overlap 168*c* may be described on a binary scale, i.e., 0 vs. 1. In other words, in such cases, third overlap 168*c* may be determined using a step function. In such cases, third overlap 168*c* may accordingly be computed using a geofence. For the purposes of this disclosure, a "geofence" or "geofenced area" is a virtual perimeter or boundary defined by geographic coordinates in a digital mapping system. Geographical coordinates may include a radius from a geographical point, proximity to a landmark, zip codes, area codes, longitude and latitude, cities, states, countries, counties, travel time, and/or the like. Geofence may be generated as a radius around a point or location (e.g., a residential address of a user and/or a location specified by query attribute 124) or using arbitrary borders drawn by user (e.g., the borders a neighborhood). In some embodiments, the point or location may be selected by a user, through one or more secondary inputs, which may include, as nonlimiting examples, tapping on a screen, inputting an address, inputting coordinates, and/or the like. Geofences may be generated to match a predetermined set of boundaries such as neighborhoods, zip codes, county, state, and city limits, area codes, voting districts, geographic regions, streets, rivers, other landmarks, and/or the like. In one or more embodiments, geofences may be generated as a function of user data 104/query data structure 120 using one or more addresses detected therein. Geofences may be used in location-based services and applications to trigger specific actions or events when a mobile device or GPS-enabled object enters, exits, or remains within a designated area. In one or more embodiments, a user interface on one or more remote devices may be updated as a function of an entity's physical presence within a geofenced area. A person of ordinary skill in the art, upon reviewing the entirety of this disclosure, will be able to recognize suitable means to implement a geofence for apparatus 100.

With continued reference to FIG. 1, in some other cases, alignment between first positional attribute 132 and second positional attribute 160 may not be a matter of preference and/or convenience, and accordingly, third overlap 168*c* may be computed on a continuous scale, such as without limitation by using an exponential decay function:

$$\text{third overlap} = e^{-(d/a)}$$

Wherein d is the distance between a first location specified by first positional attribute 132 and a second position specified by second positional attribute 160, and a is a characteristic distance specified by apparatus 100 (e.g., 500 miles). As a nonlimiting example, if a first positional attribute 132 specifies that a user is primarily residing in Boston, MA 02116, and a second positional attribute 160 of third-party data structure 108 indicates that a clinical trial is recruiting volunteers for participation within the great New England area, third overlap 168*c* may be determined as 1, which indicates a satisfactory match. As a nonlimiting example, if first positional attribute 132 specifies that a user is primarily residing in Seattle, WA 98103, and second positional attribute 160 of third-party data structure 108 indicates that a clinical trial is recruiting volunteers for participation at a facility in Portland, OR 97035, which is 188 miles away from Seattle, WA 98103, third overlap 168*c* may accordingly be determined using the exponential function described above. Specifically, assuming a characteristic distance, a, of 500 miles, third overlap may be computed as 0.69, which indicates an upper-medium-level match.

With continued reference to FIG. 1, computing overlap score 164 includes computing the overlap score 164 as a function of first overlap 168*a*, a first weight 172*a* associated with the first overlap 168*a*, second overlap 168*b*, and a second weight 172*b* associated with the second overlap 168*b*. For the purposes of this disclosure, a "weight" is a numerical factor that, when applied to a data element, increases or decreases its value in refection of its relevance, significance, priority, and/or the like. In one or more embodiments, a weight be applied as a scaling factor or multiplier, as recognized by a person of ordinary skill in the art, upon reviewing the entirety of this disclosure. In one or more embodiments, a weight may be assigned by a user and/or as a function of the urgency or flexibility associated with one or more aspects of user data 104 and/or query data structure 120. As a nonlimiting example, a user under a critical condition, such as a patient diagnosed with Stage III pancreatic cancer, may specify that a match between first temporal attribute 128 and second temporal attribute 156 is the top priority in order to enroll in a clinical trial program and receive treatment as soon as possible. In contrast, such user may focus less on a match between query attribute 124 and data feature 152, i.e., be more willing to experiment on treatments that treat cancers in general and are not necessarily targeted towards Stage III pancreatic cancer. For such a case, accordingly, apparatus 100 may assign a small weight 172*a* but a large second weight 172*b*. As another nonlimiting example, a user diagnosed with an extremely rare genetic disorder may specify that a match between query attribute 124 and data feature 152 is the top priority in order to enroll in a highly specific clinical trial program that focuses on a matching type of genetic disorder. For such a case, apparatus 100 may assign a large first weight 172*a*. Similarly, as another nonlimiting example, a user diagnosed with a chronic condition that is not life-threating, or a user with a medical condition currently under remission, may have a more flexible timeline and be willing to participate in clinical trial programs that are satisfactory matches in terms of the conditions they are intended to treat or mitigate. For such as a case, accordingly, apparatus 100 may assign a large first weight 172*a* but a small second weight 172*b*.

With continued reference to FIG. 1, in one or more embodiments, computing overlap score 164 may further include computing the overlap score 164 as a function of third overlap 168*c* and a third weight 172*c* associated with the third overlap 168*c*, consistent with details described above. In one or more embodiments, for the sake of a fair comparison in downstream processing steps, a plurality of weights may be normalized and add up to 1. In some cases, first weight 172*a* and second weight 172*b* may add up to 1. In some other cases, first weight 172*a*, second weight 172*b*, and third weight 172*c* may add up to 1. In other words, overlap score 164 may be a weighted average of first overlap 168*a*, second overlap 168*b*, and optionally third overlap 168*c*. It is worth noting that calculation of overlap score 164 may be a function of other attributes not disclosed herein that pertain to apparatus 100. A person of ordinary skill in the art, upon reviewing the entirety of this disclosure, will be able to recognize attributes that may be utilized as parameters for apparatus 100.

With continued reference to FIG. 1, in one or more embodiments, computing overlap score 164 may involve the use of a machine-learning model. Specifically, computing overlap score 164 may include receiving overlap calculation training data 176 including a plurality of exemplary overlap scores as outputs correlated with a plurality of exemplary query data structures as inputs. At least a processor 112 may be configured to iteratively train an overlap calculation machine-learning model 180 using overlap calculation training data 176, such as without limitation by adjusting a plurality of weights associated thereto, consistent with details described above. Trained overlap calculation machine-learning model 180 may subsequently be used to calculate overlap score 164. Implementation of this machine learning model may be consistent with any type of machine learning model or algorithm described in this disclosure. In one or more embodiments, overlap calculation training data may include data specifically synthesized for training purposes using one or more generative models, as described in this disclosure. In one or more embodiments, one or more datasets from previous queries may be incorporated into overlap calculation training data 176 upon validation. In one or more embodiments, overlap calculation training data 176 may be retrieved from one or more databases and/or other repositories of similar nature or be supplied as one or more inputs from one or more users. In one or more embodiments, at least a portion of overlap calculation training data 176 may be added, deleted, replaced, or otherwise updated as a function of one or more inputs from one or more users. A person of ordinary skill in the art, upon reviewing the entirety of this disclosure, will be able to recognize suitable means to implement overlap calculation machine-learning model 180 in apparatus 100.

With continued reference to FIG. 1, in one or more embodiments, identifying the one or more matches, as described above, may include comparing overlap score 164 with one or more matching thresholds 184 and identifying the one or more matches as a function of the comparison. For the purposes of this disclosure, a "matching threshold" is a numerical threshold at or beyond which one data element can be considered a match with respect to another data element. In some cases, matching threshold 184 may be specified by a user in user data 104 or supplied by a user as secondary user data 104, as described in detail below. As a nonlimiting example, a user may specify that a minimum overlap score of 0.8 is needed for one or more third-party data structures 108 to be considered a match, and apparatus 100 may subsequently query data repository 148 and return 1,000 third-party data structures 108 that meet such requirement. The user may be prompted to revise matching threshold 184, such as without limitation by submitting secondary user data, to increase its value from 0.8 to 0.9, thereby further filtering third-party data structures 108 to isolate the more suitable portion thereof. As another nonlimiting example, a user may specify that a minimum overlap score of 0.9 is needed for one or more third-party data structures 108 to be considered a match, and apparatus 100 may subsequently query data repository 148 and return only 5 third-party data structures 108 that meet such requirement. The user may be prompted to revise matching threshold 184, such as without limitation by submitting secondary user data, to decrease its value from 0.9 to 0.6, thereby relaxing the search criteria and identify additional third-party data structures 108 that, while not being the best match, may still be sufficiently compatible with user data 104. In some cases, matching threshold 184 may be automatically assigned and dynamically updated by apparatus 100 based on an outcome of query, with minimum or no human intervention, consistent with details described above. In some cases, in order to pair a user/user data 104 with one or more third-party data structures 108, at least a processor 112 may be configured to suggest certain modifications to user data 104 and/or one or more elements therein to repeat the query step, until a satisfactory number of matches is identified. As a nonlimiting example, at least a processor 112 may suggest that a user remove certain potentially flexible criteria or preferences from user data 104/query data structure 120, such as without limitation "for female only", "for 65 years or above only", "within a 50-mile radius from city X only", "active between date A and date B only", or the like, in order to include third-party data structures 108 pertaining to a broader spectrum of genders, age groups, locations, and/or time spans, among others. In some cases, comparing overlap score 164 with one or more matching thresholds 184 may include comparing individual overlaps 168*a-c* upon which overlap score 164 is computed, as described above, with one or more corresponding matching thresholds 184. As a non-limiting example, such comparison may be implemented using a fuzzy set comparison, as described in further detail below in this disclosure.

With continued reference to FIG. 1, a list containing identified one or more matching third-party data structures 108 may be further filtered, ranked, rearranged, or otherwise processed. In one or more embodiments, each third-party data structure 108 of plurality of third-party data structures 108 may be associated with a positivity metric 188. For the purposes of this disclosure, a "positivity metric" is a metric describing the likelihood of a successful conclusion or a positive outcome pertaining to one or more aspects of a third-party data structure 108 and/or one or more entities related thereto. For the case of a clinical trial program, one or more new drugs or therapies may be currently under clinical trial or scheduled for a clinical trial. In such a case, a positivity metric may include a success rate associated with similar drugs or therapies in previous clinical trial programs. These drugs or therapies may be intended to treat the same or a similar condition or set of conditions. Additionally, and/or alternatively, these drugs or therapies may belong to the same class and/or associated to the same core chemical structure (i.e., pharmacophore) as the new drugs or therapies. Therefore, historical data associated with concluded clinical trial programs may provide valuable insights regarding the likely outcome of pending clinical trial programs. In some cases, such historical data may be retrieved from one or more proprietary databases communicatively connected to apparatus 100. Similarly, in some cases, a positivity metric may include a success rate of previous clinical trials based on the organization, company, brand, or the like associated thereto. Accordingly, identifying the one or more matches may include filtering plurality of third-party data structures 108 as a function of positivity metric 188 and updating the identified one or more matches as a function of the filtered plurality of third-party data structures 108.

With continued reference to FIG. 1, in one or more embodiments, querying data repository 148 may include identifying one or more prior users associated with at least a third-party data structure 108 of the plurality of third-party data structures 108. Upon obtaining permission from these prior users, they may be paired with a user to share their experience. For the case of a clinical trial, such design may support a community of patients who have gone through or are currently undergoing similar challenges and help a user gain hope, inspiration, strategies, insights, or the like from their peers.

With continued reference to FIG. 1, at least a processor 112 is further configured to generate a recommended course of action 192 as a function of the one or more matches. For the purposes of this disclosure, a "recommended course of action" is a single action or a series of actions to be taken or performed by a user. A recommended course of action may include any format pertaining to a delivery of information, a performance of activity, and/or the like, that is deemed relevant to apparatus 100 by a person of ordinary skill in the art, upon reviewing the entirety of this disclosure. In one or more embodiments, recommended course of action 192 may include a recommendation of one or more suitable clinical trial programs for a user, consistent with details described above. Additionally, and/or alternatively, in one or more embodiments, recommended course of action 192 may include a treatment plan and/or a personalized medical solution.

With continued reference to FIG. 1, in one or more embodiments, at least a processor is further configured to receive secondary user data 104. Such secondary user data 104 may include user feedback explicitly provided by a user or status data automatically detected by at least a processor 112. In some cases, such secondary user data 104 may include real-time user data generated after an inception of a clinical trial program. At least a processor 112 may accordingly be configured to modify query data structure 120 as a function of secondary user data 104 and/or update data repository 148 as a function of the modified query data structure 120.

With continued reference to FIG. 1, in one or more embodiments, at least a processor 112 may implement one or more aspects of "generative artificial intelligence (AI)", a type of AI that uses machine-learning algorithms to create, establish, or otherwise generate data such as, without limitation, interpretations of medical data. In one or more embodiments, machine-learning module described below in this disclosure may generate one or more generative machine-learning models that are trained on one or more prior iterations. One or more generative machine-learning models may be configured to generate new examples that are similar to the training data of the one or more generative machine-learning models but are not exact replicas; for instance, and without limitation, data quality or attributes of the generated examples may bear a resemblance to the training data provided to one or more generative machine-learning models, wherein the resemblance may pertain to underlying patterns, features, or structures found within the provided training data.

With continued reference to FIG. 1, in some cases, generative machine-learning models may include one or more generative models. For the purposes of this disclosure, a "generative model" is a statistical model of joint probability distribution $P(X,Y)$ between a given observable variable, x, and a target variable, y. x may represent features or data that can be directly measured or observed, whereas y may represent outcomes or labels that one or more generative models aim to predict or generate. Exemplary generative models include generative adversarial models (GANs), diffusion models, and the like. In one or more embodiments, generative models may rely on Bayes theorem to find joint probability; for instance, and without limitation, naive Bayes classifiers may be employed by computing device to categorize input data such as without limitation user data 104 and/or elements therein.

With continued reference to FIG. 1, in a nonlimiting example, one or more generative machine-learning models may include one or more naive Bayes classifiers generated, by processor 112, using a naive Bayes classification algorithm. Naive Bayes classification algorithm may generate classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as $P(A/B)=P(B/A) \times P(A) \div P(B)$, where $P(A/B)$ is the probability of hypothesis A given data B, also known as posterior probability; $P(B/A)$ is the probability of data B given that the hypothesis A was true; $P(A)$ is the probability of hypothesis A being true regardless of data, also known as prior probability of A; and $P(B)$ is the probability of data regardless of the hypothesis. A naive Bayes algorithm may be generated by first transforming training data into a frequency table. Processor 112 and/or computing device may then calculate a likelihood table by computing probabilities of different data entries and classification labels. Processor 112 and/or computing device may utilize a naive Bayes equation to calculate a posterior probability for each class. A class containing the highest posterior probability is the outcome of prediction.

With continued reference to FIG. 1, although naive Bayes classifier may be primarily known as a probabilistic classification algorithm; however, it may also be considered a generative model described herein due to its capability of modeling the joint probability distribution $P(X,Y)$ over observable variables, X, and target variable, Y. In one or more embodiments, naive Bayes classifier may be configured to make an assumption that the features, X, are conditionally independent given class label, Y, allowing generative model to estimate a joint distribution as $P(X,Y)=P(Y)\Pi_i P(X_i|Y)$, wherein $P(Y)$ is the prior probability of the class, and $P(X_i|Y)$ is the conditional probability of each feature given the class. One or more generative machine-learning models containing naive Bayes classifiers may be trained on labeled training data, estimating conditional probabilities $P(X_i|Y)$ and prior probabilities $P(Y)$ for each class; for instance, and without limitation, using techniques such as Maximum Likelihood Estimation (MLE). One or more generative machine-learning models containing naive Bayes classifiers may select a class label, y, according to prior distribution, $P(Y)$, and for each feature, $X_i$, sample at least a value according to conditional distribution, $P(X_i|y)$. Sampled feature values may then be combined to form one or more new data instances with selected class label, y. In a nonlimiting example, one or more generative machine-learning models may include one or more naive Bayes classifiers to generate new examples, as a function of exemplary input data or classes of input data, wherein the models may be pretrained and/or retrained using a plurality of features as input correlated to plurality of labelled classes as outputs.

With continued reference to FIG. 1, in one or more embodiments, one or more generative machine-learning models may include generative adversarial network (GAN). For the purposes of this disclosure, a "generative adversarial network" is a type of artificial neural network with at least two sub models (i.e., neural networks), a generator and a discriminator, that compete against each other in a process that ultimately results in the generator learning to generate new data samples, wherein the "generator" is a component of the GAN that learns to create hypothetical data by incorporating feedback from the "discriminator" configured to distinguish real data from the hypothetical data. In one or more embodiments, generator may learn to make discriminator classify its output as real. In one or more embodiments, discriminator may include a supervised machine-learning model while generator may include an unsupervised machine-learning model, as described in further detail below.

With continued reference to FIG. 1, in one or more embodiments, discriminator may include one or more discriminative models, i.e., models of conditional probability $P(Y|X=x)$ of target variable, Y, given observed variable, X. In one or more embodiments, discriminative models may learn boundaries between classes or labels in given training data. In a nonlimiting example, discriminator may include one or more classifiers as described in further detail below to distinguish between different categories, e.g., real vs. fake, or states, e.g., TRUE vs. FALSE within the context of generated data. In one or more embodiments, processor 112 may implement one or more classification algorithms such as, without limitation, Support Vector Machines (SVM), Logistic Regression, Decision Trees, and/or the like to define decision boundaries.

With continued reference to FIG. 1, additionally, or alternatively, one or more generative models may also include a variational autoencoder (VAE). For the purposes of this disclosure, a "variational autoencoder" is an autoencoder or an artificial neural network architecture whose encoding distribution is regularized during the model training process in order to ensure that its latent space includes desired properties allowing new data sample generation. In one or more embodiments, VAE may include a prior and noise distribution respectively, trained using expectation-maximization meta-algorithms such as, without limitation, probabilistic PCA, sparse coding, among others. In a nonlimiting example, VAE may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from latent space to input space.

With continued reference to FIG. 1, in a nonlimiting example, VAE may be used by processor 112 and/or computing device to model complex relationships between various parts of a dataset. In some cases, VAE may encode input data into a latent space, capturing one or more nuanced parameters therein. Such encoding process may include learning one or more probabilistic mappings from observed design models to a lower-dimensional latent representation. Latent representation may then be decoded back into the original data space, therefore reconstructing the design model. In some cases, such decoding process may allow VAE to generate new examples or variations that are consistent with the learned distributions.

With continued reference to FIG. 1, other exemplary embodiments of generative machine-learning models may include, without limitation, long short-term memory networks (LSTMs), (generative pre-trained) transformer (GPT) models, mixture density networks (MDN), and/or the like. A person of ordinary skill in the art, upon reviewing the entirety of this disclosure, will be aware of various generative machine-learning models that may be used to perform certain function or functions of apparatus 100 as described herein.

With continued reference to FIG. 1, in one or more embodiments, machine-learning module may be further configured to generate a multimodal neural network that combines various neural network architectures described herein. In a nonlimiting example, multimodal neural network may combine LSTM for time-series analysis with GPT models for natural language processing. Such fusion may be applied by at least a processor 112 and/or computing device to generate new data or data structures. In one or more embodiments, multimodal neural network may also include a hierarchical multimodal neural network, wherein the hierarchical multimodal neural network may involve a plurality of layers of integration. For instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multimodal neural network may include, without limitation, ensemble-based multimodal neural network, cross-modal fusion, adaptive multimodal network, among others. A person of ordinary skill in the art, upon reviewing the entirety of this disclosure, will be aware of various multimodal neural networks and combination thereof that may be implemented by apparatus 100 in accordance with this disclosure.

With continued reference to FIG. 1, in one or more embodiments, processor 112 may perform one or more functions of apparatus 100 by using optical character recognition (OCR) to read digital files and extract information therein. In one or more embodiments, OCR may include automatic conversion of images (e.g., typed, handwritten, or printed text) into machine-encoded text. In one or more embodiments, recognition of at least a keyword from an image component may include one or more processes, including without limitation OCR, optical word recognition, intelligent character recognition, intelligent word recognition, and the like. In one or more embodiments, OCR may recognize written text one glyph or character at a time, for example, for languages that use a space as a word divider. In one or more embodiments, intelligent character recognition (ICR) may recognize written text one glyph or character at a time, for instance by employing machine-learning processes. In one or more embodiments, intelligent word recognition (IWR) may recognize written text, one word at a time, for instance by employing machine-learning processes.

With continued reference to FIG. 1, in one or more embodiments, OCR may employ preprocessing of image components. Preprocessing process may include without limitation de-skew, de-speckle, binarization, line removal, layout analysis or "zoning", line and word detection, script recognition, character isolation or "segmentation", and normalization. In one or more embodiments, a de-skew process may include applying a transform (e.g., homography or affine transform) to an image component to align text. In one or more embodiments, a de-speckle process may include removing positive and negative spots and/or smoothing edges. In one or more embodiments, a binarization process may include converting an image from color or greyscale to black-and-white (i.e., a binary image). Binarization may be performed as a simple way of separating text (or any other desired image component) from the background of image component. In one or more embodiments, binarization may be required for example if an employed OCR algorithm only works on binary images. In one or more embodiments, line removal process may include removal of non-glyph or non-character imagery (e.g., boxes and lines). In one or more embodiments, a layout analysis or "zoning" process may identify columns, paragraphs, captions, and the like as distinct blocks. In one or more embodiments, a line and word detection process may establish a baseline for word and character shapes and separate words, if necessary. In one or more embodiments, a script recognition process may, for example in multilingual documents, identify a script, allowing an appropriate OCR algorithm to be selected. In one or more embodiments, a character isolation or "segmentation" process may separate signal characters, for example, character-based OCR algorithms. In one or more embodiments, a normalization process may normalize the aspect ratio and/or scale of image component.

With continued reference to FIG. 1, in one or more embodiments, an OCR process may include an OCR algorithm. Exemplary OCR algorithms include matrix-matching processes and/or feature extraction processes. Matrix matching may involve comparing an image to a stored glyph on a pixel-by-pixel basis. In one or more embodiments, matrix matching may also be known as "pattern matching", "pattern recognition", and/or "image correlation". Matrix matching may rely on an input glyph being correctly isolated from the rest of image component. Matrix matching may also rely on a stored glyph being in a similar font and at the same scale as input glyph.

With continued reference to FIG. 1, in one or more embodiments, an OCR process may include a feature extraction process. In one or more embodiments, feature extraction may decompose a glyph into features. Exemplary nonlimiting features may include corners, edges, lines, closed loops, line direction, line intersections, and the like. In one or more embodiments, feature extraction may reduce the dimensionality of representation and may make the recognition process computationally more efficient. In one or more embodiments, extracted features can be compared with an abstract vector-like representation of a character, which might be reduced to one or more glyph prototypes. General techniques of feature detection in computer vision are applicable to this type of OCR. In one or more embodiments, machine-learning process like nearest neighbor classifiers (e.g., k-nearest neighbors algorithm) can be used to compare image features with stored glyph features and choose a nearest match. OCR may employ any machine-learning process described in this disclosure. Exemplary nonlimiting OCR software includes Cuneiform and Tesseract. Cuneiform is a multi-language, open-source OCR system originally developed by Cognitive Technologies of Moscow, Russia. Tesseract is a free OCR software originally developed by Hewlett-Packard of Palo Alto, California, United States.

With continued reference to FIG. 1, in one or more embodiments, OCR may employ a two-pass approach to character recognition. Second pass may include adaptive recognition and use letter shapes recognized with high confidence on a first pass to better recognize remaining letters on a second pass. In one or more embodiments, two-pass approach may be advantageous for unusual fonts or low-quality image components where visual verbal content may be distorted. Another exemplary OCR software tool includes OCRopus. The development of OCRopus is led by the German Research Center for Artificial Intelligence in Kaiserslautern, Germany. In one or more embodiments, OCR software may employ neural networks, for example, deep neural networks, as described in this disclosure below.

With continued reference to FIG. 1, in one or more embodiments, OCR may include post-processing. For example, OCR accuracy can be increased, in some cases, if output is constrained by a lexicon. A lexicon may include a list or set of words that are allowed to occur in a document. In one or more embodiments, a lexicon may include, for instance, all the words in the English language, or a more technical lexicon for a specific field. In some cases, an output stream may be a plain text stream or file of characters. In one or more embodiments, an OCR may preserve an original layout of visual verbal content. In one or more embodiments, near-neighbor analysis can make use of co-occurrence frequencies to correct errors by noting that certain words are often seen together. For example, "Washington, D.C." is generally far more common in English than "Washington DOC". In one or more embodiments, an OCR process may make use of a priori knowledge of grammar for a language being recognized. For example, OCR process may apply grammatical rules to help determine if a word is likely to be a verb or a noun. Distance conceptualization may be employed for recognition and classification. For example, a Levenshtein distance algorithm may be used in OCR post-processing to further optimize results. A person of ordinary skill in the art will recognize how to apply the aforementioned technologies to extract information from a digital file upon reviewing the entirety of this disclosure.

With continued reference to FIG. 1, in one or more embodiments, a computer vision module configured to perform one or more computer vision tasks such as, without limitation, object recognition, feature detection, edge/corner detection thresholding, or machine-learning process may be used to recognize specific features or attributes. For the purposes of this disclosure, a "computer vision module" is a computational component designed to perform one or more computer vision, image processing, and/or modeling tasks. In one or more embodiments, computer vision module may receive one or more digital files from a data repository and generate one or more labels therefrom.

With continued reference to FIG. 1, in one or more embodiments, computer vision module may include an image processing module, wherein images may be pre-processed using the image processing module. For the purposes of this disclosure, an "image processing module" is a component designed to process digital images such as images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate one or more labels and/or recognize one or more reference attributes, one or more image processing tasks, such as noise reduction, contrast enhancement, intensity normalization, image segmentation, and/or the like, may be performed by computer vision module on a plurality of images to isolate certain features or components from the rest. In one or more embodiments, one or more machine-learning models may be used to perform segmentations, for example, and without limitation, a U-net (i.e., a convolution neural network containing a contracting path as an encoder and an expansive path as a decoder, wherein the encoder and the decoder forms a U-shaped structure). A person of ordinary skill in the art, upon reviewing the entirety of this disclosure, will be aware of various image processing, computer vision, and modeling tasks that may be performed by processor 112.

With continued reference to FIG. 1, in one or more embodiments, one or more functions of apparatus 100 may involve a use of image classifiers to classify images within any data described in this disclosure. For the purposes of this disclosure, an "image classifier" is a machine-learning model that sort inputs of image information into categories or bins of data, outputting the categories or bins of data and/or labels associated therewith. Image classifier may include a mathematical model, a neural net, or a program generated by a machine-learning algorithm known as a "classification algorithm", as described in further detail below. Image classifier may be configured to output at least a datum that labels or otherwise identifies a set of images that are clustered together, found to be close under a distance metric as described below, or the like. Computing device and/or another device may generate image classifier using a classification algorithm. For the purposes of this disclosure, a classification algorithm is a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, processor 112 may use image classifier to identify a key image in any data described in this disclosure. For the purposes of this disclosure, a "key image" is an element of visual data used to identify and/or match elements to each other. Image classifier may be trained with binarized visual data that have already been classified to determine key images in any other data described in this disclosure. For the purposes of this disclosure, "binarized visual data" are visual data that are described in a binary format. For example, binarized visual data of a photo may comprise ones and zeroes, wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data described in this disclosure and output a key image with the data. In one or more embodiments, image classifier may be used to compare visual data in one data set with visual data in another data set, as described below.

With continued reference to FIG. 1, processor 112 may be configured to perform feature extraction on user data. For the purposes of this disclosure, "feature extraction" is a process of transforming an initial data set into informative measures and values. In one or more embodiments, feature extraction may be used to determine one or more spatial relationships within a drawing that may be used to uniquely identify one or more features. In one or more embodiments, processor 112 may be configured to extract one or more regions of interest, wherein the regions of interest may be used to extract one or more features using one or more feature extraction techniques.

With continued reference to FIG. 1, at least a processor 112 may be configured to perform one or more of its functions using a feature learning algorithm. For the purposes of this disclosure, a "feature learning algorithm" is a machine-learning algorithm that identifies associations between elements of data in a data set where particular outputs and/or inputs are not specified. Data set may include without limitation a training data set. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1, feature learning and/or clustering algorithm may be implemented, as a non-limiting example, using a k-means clustering algorithm. For the purposes of this disclosure, a "k-means clustering algorithm" is a type of cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering, whereby observations or unclassified cluster data entries that belong to a child cluster also belong to a parent cluster.

With continued reference to FIG. 1, computing device may generate a k-means clustering algorithm by receiving unclassified data and outputting a definite number of classified data entry clusters, wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by computing k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, which may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\mathrm{argmin}_{ci \in C} \, \mathrm{dist}(ci,x)^2$, where argmin includes argument of the minimum, ci includes a collection of centroids in a set C, and dist includes standard Euclidean distance. K-means clustering module may then recompute centroids by taking a mean of all cluster data entries assigned to a centroid's cluster. This may be calculated based on $ci=1/|Si|\Sigma xi \in Si^{xi}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. For the purposes of this disclosure, a "degree of similarity index value" is a distance measured between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between the element to be compared and/or clustered and a particular cluster.

With continued reference to FIG. 1, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively, or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skills in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1, in one or more embodiments, processor 112 may use an image recognition algorithm to determine patterns within an image. In one or more embodiments, image recognition algorithm may include an edge-detection algorithm, which may detect one or more shapes defined by edges. For the purposes of this disclosure, an "edge detection algorithm" is or includes a mathematical method that identifies points in a digital image at which the image brightness changes sharply and/or has discontinuities. In one or more embodiments, such points may be organized into straight and/or curved line segments, which may be referred to as "edges". Edge detection may be performed using any suitable edge detection algorithm, including without limitation Canny edge detection, Sobel operator edge detection, Prewitt operator edge detection, Laplacian operator edge detection, and/or differential edge detection. Edge detection may include phase congruency-based edge detection, which finds all locations of an image where all sinusoids in the frequency domain, for instance when generated using a Fourier decomposition, may have matching phases which may indicate a location of an edge.

With continued reference to FIG. 1, apparatus 100 may further include or be communicatively connected to a display device. For the purposes of this disclosure, a "display device" is a device configured to show visual information. In some cases, display device may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer-generated images and/or information. In one or more embodiments, display device may be configured to visually present data through a user interface or a graphical user interface (GUI) to at least a user, wherein the user may interact with the data through the user interface or GUI, as described below. In one or more embodiments, a user may view GUI through display device. In one or more embodiments, display device may be located on a remote device, as described below. Additional details will be provided below in this disclosure through nonlimiting examples.

With continued reference to FIG. 1, display device may include a remote device. For the purposes of this disclosure, a "remote device" is a computer device separate and distinct from apparatus 100. For example, and without limitation, a remote device may include a smartphone, a tablet, a laptop, a desktop computer, or the like. In one or more embodiments, a remote device may be communicatively connected to apparatus 100 such as, for example, through network communication, through Bluetooth communication, and/or the like. In one or more embodiments, processor 112 may receive user data 104 and/or initiate one or more of subsequent steps through a remote device. In one or more embodiments, one or more inputs from one or more users may be submitted through a user interface, such as a GUI, displayed using a remote device, as described below.

With continued reference to FIG. 1, in one or more embodiments, apparatus 100 may further include a user interface. In one or more embodiments, recommended course of action 192 or the like may be displayed using a user interface. For the purposes of this disclosure, a "user interface" is a means by which a user and a computer system interact, for example, using input devices and software. A user interface may include a graphical user interface (GUI), command line interface (CLI), menu-driven user interface, touch user interface, voice user interface (VUI), form-based user interface, any combination thereof, or the like. In one or more embodiments, a user may interact with a user interface using computing device distinct from and communicatively connected to apparatus 100 and/or processor 112, such as a smartphone, tablet, or the like operated by the user. A user interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, a GUI may include icons, menus, other visual indicators or representations (graphics), audio indicators such as primary notation, display information, and related user controls. A menu may contain a list of choices and may allow users to select one from them. A menu bar may be displayed horizontally across the screen as a pull-down menu. A menu may include a context menu that appears only when user performs a specific action. Files, programs, web pages, and the like may be represented using a small picture within a GUI. In one or more embodiments, a GUI may include a graphical visualization of a user profile and/or the like. In one or more embodiments, processor 112 may be configured to modify and/or update a GUI as a function of at least an input or the like by populating a user interface data structure and visually presenting data through modification of the GUI.

With continued reference to FIG. 1, in one or more embodiments, a GUI may contain one or more interactive elements. For the purposes of this disclosure, an "interactive element" is an element within a GUI that allows for communication with processor 112 by one or more users. For example, and without limitation, interactive elements may include a plurality of tabs wherein selection of a particular tab, such as for example, by using a fingertip, may indicate to a system to perform a particular function and display the result through a GUI. In one or more embodiments, interactive element may include tabs within a GUI, wherein the selection of a particular tab may result in a particular function. In one or more embodiments, interactive elements may include words, phrases, illustrations, and the like to indicate a particular process that one or more users would like a system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 1, in one or more embodiments, display device and/or remote device may be configured to display at least an event handler graphic corresponding to at least an event handler. For the purposes of this disclosure, an "event handler graphic" is a graphical element with which user interacts using display device and/or remote device to enter data, such as without limitation user data 104 or the like as described above. Event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on display device and/or remote device in response to one or more user inputs. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. An event handler may generate prompts for further information, may compare data to validation rules such as requirements that the data in question be entered within certain numerical ranges, and/or may modify data and/or generate warnings to user in response to such requirements. An event handler may convert data into expected and/or desired formats, for instance such as date formats, currency entry formats, name formats, or the like. An event handler may transmit data from a remote device to apparatus 100, processor 112, and/or computing device.

With continued reference to FIG. 1, in one or more embodiments, an event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, cross-session state variable data may represent a search that user entered in a past session. Cross-session state variable may be saved using any suitable combination of client-side data storage on a remote device and server-side data storage on a computing device; for instance, data may be saved wholly or in part as a "cookie" which may include data or an identification of remote device to prompt provision of cross-session state variable by the computing device, which may store the data on the computing device. Alternatively, or additionally, computing device may use login credentials, device identifier, and/or device fingerprint data to retrieve cross-session state variable, which the computing device may transmit to remote device. Cross-session state variable may include at least a prior session datum. A prior session datum may include any element of data that may be stored in cross-session state variable. An event handler graphic may be further configured to display at least a prior session datum, for instance and without limitation, by auto-populating user query data from previous sessions.

With continued reference to FIG. 1, in one or more embodiments, processor 112 and/or computing device may configure display device and/or remote device to generate a graphical view. For the purposes of this disclosure, a "graphical view" is a data structure that results in display of one or more graphical elements on a screen. A graphical view may include at least a display element. For the purposes of this disclosure, a "display element" is an image that a program and/or data structure cause to be displayed. Display elements may include, without limitation, windows, pop-up boxes, web browser pages, display layers, and/or any other display element deemed relevant by a person of ordinary skill in the art upon reviewing the entirety of this disclosure. A graphical view may include at least a selectable event graphic corresponding to one or more selectable event handlers. For the purposes of this disclosure, a "selectable event graphic" is a graphical element that, upon selection, will trigger an action to be performed. Selection may be performed using a cursor or other locator as manipulated using a locator device such as a mouse, touchscreen, track pad, joystick, or the like. As a nonlimiting example, a selectable event graphic may include a redirection link. For the purposes of this disclosure, a redirection link is a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of a selectable event graphic. Redirection may be performed using any event handler, including without limitation event handlers detecting the click of a mouse or other locator, access of redirection link using a touchscreen, the selection of any key, mouseover events, or the like.

With continued reference to FIG. 1, it should be noted that apparatus 100 and related methods described herein are not limited to identification of clinical trial programs only. For example, and without limitation, data-matching capabilities disclosed herein may be effectively adapted for use within other contexts involving complex data structures. A person of ordinary skill in the art, upon reviewing the entirety of this disclosure, will recognize one or more embodiments described herein (although principally focused identification of clinical trial programs) and their underlaying principles may be readily transferrable to a broader spectrum of applications such as without limitation identification of educational resources or degree programs, mediation of business transactions, delegation and management of workloads, outsourcing of customized mechanical parts for manufacture, among others, that are not currently disclosed.

Referring now to FIG. 2, an exemplary workflow 200 for computing an overlap score 164 is illustrated. in one or more embodiments involving more complex data structures, attributes of user data 104 may not necessarily have a one-to-one correlation with attributes of third-party data structure 108. Instead, an attribute of user data 104 may be related to a plurality of attributes of third-party data structure 108, and vice versa. Accordingly, computing one or more overlaps/overlap score 164 may include computing the one or more overlaps/overlap score 164 by multiplication of matrices. In some cases, a plurality of attributes pertaining to query data structure 120 ($Q_{11}$-$Q_{nn}$), such as without limitation query attribute 124, first temporal attribute, and/or first positional attribute 132, may be represented by a first matrix 204; similarly, a plurality of attributes pertaining to third-party data structure 108 ($F_{11}$-$F_{nn}$), such as without limitation data feature 152, second temporal attribute 156, and/or second positional attribute 160, may be represented by a second matrix 208. Accordingly, overlaps may be computed by multiplying first matrix 204 with second matrix 208. In some cases, a plurality of weights ($W_{11}$-$W_{nn}$), e.g., first weight 172a, second weight 172b, third weight 172c, and the like, may be represented by a third matrix 212 correlated with different combinations between attributes in first matrix 204 and attributes in second matrix 208. Accordingly, overlap score 164 may be computed by multiplying first matrix 204, the second matrix 208, and the third matrix 212.

Figure 3:
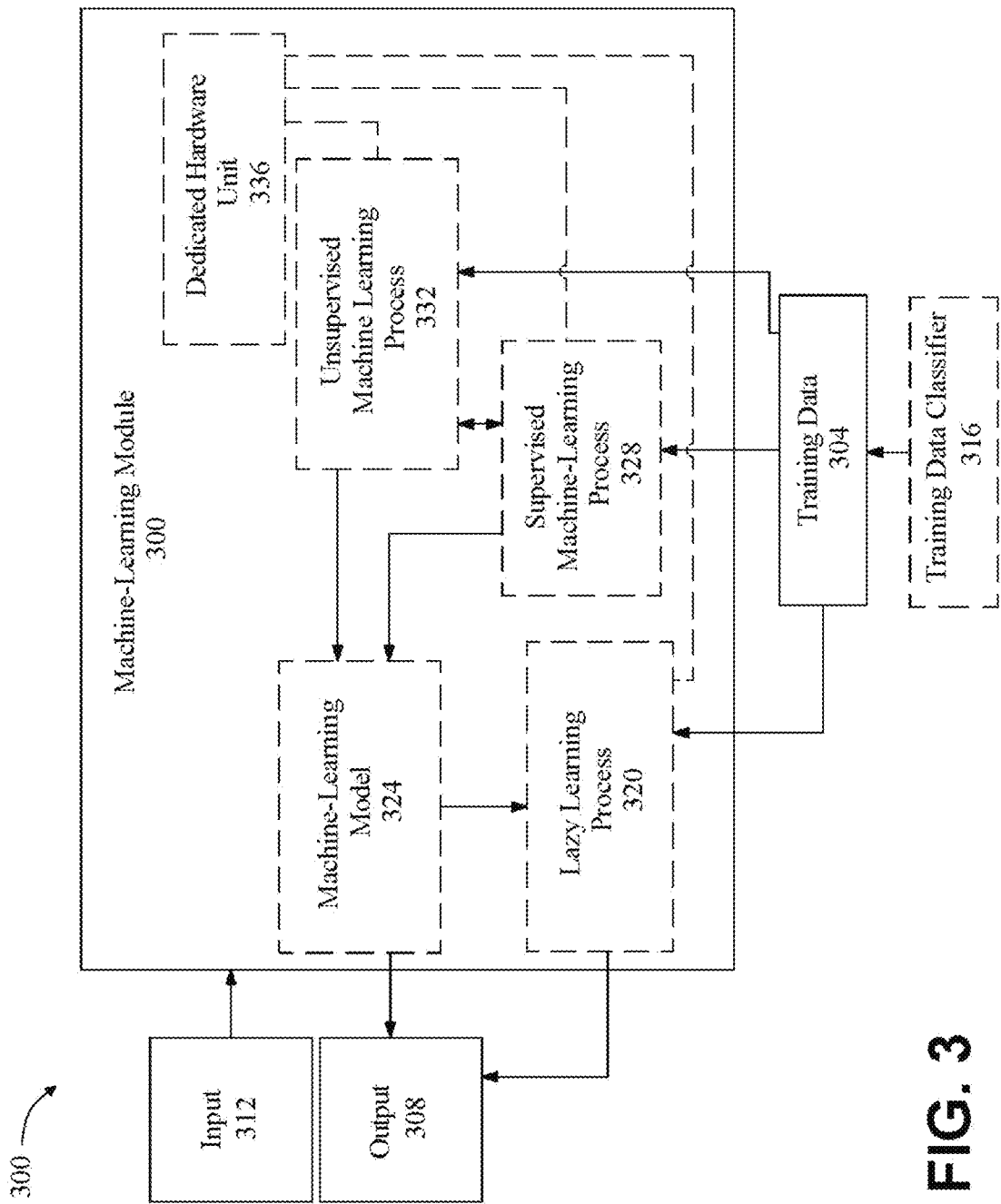
FIG. 3 is a block diagram of an exemplary embodiment of a machine-learning process.

Referring now to FIG. 3, an exemplary embodiment of a machine-learning module 300 that may perform one or more machine-learning processes as described above is illustrated. Machine-learning module may perform determinations, classification, and/or analysis steps, methods, processes, or the like as described in this disclosure using machine-learning processes. For the purposes of this disclosure, a "machine-learning process" is an automated process that uses training data 304 to generate an algorithm instantiated in hardware or software logic, data structures, and/or functions that will be performed by a computing device/module to produce outputs 308 given data provided as inputs 312. This is in contrast to a non-machine-learning software program where the commands to be executed are predetermined by user and written in a programming language.

With continued reference to FIG. 3, "training data", for the purposes of this disclosure, are data containing correlations that a machine-learning process uses to model relationships between two or more categories of data elements. For instance, and without limitation, training data 304 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a nonlimiting example, training data 304 may include data entered in standardized forms by persons or processes, such that entry of a given data element within a given field in a given form may be mapped to one or more descriptors of categories. Elements in training data 304 may be linked to descriptors of categories by tags, tokens, or other data elements. For instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 3, alternatively, or additionally, training data 304 may include one or more elements that are uncategorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a nonlimiting illustrative example, inputs may include exemplary user data 104, whereas outputs may include exemplary query data structures.

With continued reference to FIG. 3, training data 304 may be filtered, sorted, and/or selected using one or more supervised and/or unsupervised machine-learning processes and/or models as described in further detail below; such processes and/or models may include without limitation a training data classifier 316. For the purposes of this disclosure, a "classifier" is a machine-learning model that sorts inputs into categories or bins of data, outputting the categories or bins of data and/or labels associated therewith. Machine-learning model may include without limitation a data structure representing and/or using a mathematical model, neural net, or a program generated by a machine-learning algorithm, known as a "classification algorithm". A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm. For the purposes of this disclosure, a "classification algorithm" is a process wherein a computing device and/or any module and/or component operating therein derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 316 may classify elements of training data to a plurality of cohorts as a function of certain features or traits.

With continued reference to FIG. 3, machine-learning module 300 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as $P(A/B)=P(B/A) \times P(A) \div P(B)$, where $P(A/B)$ is the probability of hypothesis A given data B, also known as posterior probability; $P(B/A)$ is the probability of data B given that the hypothesis A was true; $P(A)$ is the probability of hypothesis A being true regardless of data, also known as prior probability of A; and $P(B)$ is the probability of the data regardless of the hypothesis. A naive Bayes algorithm may be generated by first transforming training data into a frequency table. Machine-learning module 300 may then calculate a likelihood table by computing probabilities of different data entries and classification labels. Machine-learning module 300 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 3, machine-learning module 300 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 304 and to classify input data to one or more clusters and/or categories of features as represented in training data 304. This may be performed by representing both training data 304 and input data in vector forms and using one or more measures of vector similarity to identify classifications within training data 304 and determine a classification of input data. K-nearest neighbors algorithm may include specifying a k-value, or a number directing the classifier to select the k most similar entries of training data 304 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 312 and elements of training data 304. Heuristic may include selecting some number of highest-ranking associations and/or training data elements.

With continued reference to FIG. 3, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may alternatively, or additionally, be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute l as derived using a Pythagorean norm:

$$l = \sqrt{\sum_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 304 are represented by different quantities of samples, which may result in proportionally equivalent vectors with divergent values.

With continued reference to FIG. 3, training examples for use as training data may be selected from a population of potential examples according to cohorts relevant to an analytical problem to be solved, a classification task, or the like. Alternatively, or additionally, training data 304 may be selected to span a set of likely circumstances or inputs for a machine-learning model and/or process to encounter when deployed. For instance, and without limitation, for each category of input data to a machine-learning model and/or process that may exist in a range of values in a population of phenomena such as images, user data, process data, physical data, or the like, a computing device, processor 112, and/or machine-learning module 300 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively, or additionally, a set of training examples may be compared to a collection of representative values in a database and/or presented to user, so that a process can detect, automatically or via user input, one or more values that are not included in the set of training examples. Computing device, processor 112, and/or machine-learning module 300 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 3, computing device, processor 112, and/or machine-learning module 300 may be configured to preprocess training data 304. For the purposes of this disclosure, "preprocessing" training data is a process that transforms training data from a raw form to a format that can be used for training a machine-learning model. Preprocessing may include sanitizing, feature selection, feature scaling, data augmentation and the like.

With continued reference to FIG. 3, computing device, processor 112, and/or machine-learning module 300 may be configured to sanitize training data. For the purposes of this disclosure, "sanitizing" training data is a process whereby training examples that interfere with convergence of a machine-learning model and/or process are removed to yield a useful result. For instance, and without limitation, a training example may include an input and/or output value that is an outlier from typically encountered values, such that a machine-learning algorithm using the training example will be skewed to an unlikely range of input 312 and/or output 308; a value that is more than a threshold number of standard deviations away from an average, mean, or expected value, for instance, may be eliminated. Alternatively, or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 3, in one or more embodiments, images used to train an image classifier or other machine-learning model and/or process that takes images as inputs 312 or generates images as outputs 308 may be rejected if image quality is below a threshold value. For instance, and without limitation, computing device, processor 112, and/or machine-learning module 300 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 3, computing device, processor 112, and/or machine-learning module 300 may be configured to precondition one or more training examples. For instance, and without limitation, where a machine-learning model and/or process has one or more inputs 312 and/or outputs 308 requiring, transmitting, or receiving a certain number of bits, samples, or other units of data, one or more elements of training examples to be used as or compared to inputs 312 and/or outputs 308 may be modified to have such a number of units of data. In one or more embodiments, computing device, processor 112, and/or machine-learning module 300 may convert a smaller number of units, such as in a low pixel count image, into a desired number of units by upsampling and interpolating. As a nonlimiting example, a low pixel count image may have 100 pixels, whereas a desired number of pixels may be 128. Processor 112 may interpolate the low pixel count image to convert 100 pixels into 128 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 312 and/or outputs 308 and corresponding inputs 312 and/or outputs 308 downsampled to smaller numbers of units, and a neural network or another machine-learning model that is trained to predict interpolated pixel values using the training data 304. As a nonlimiting example, a sample input 312 and/or output 308, such as a sample picture, with sample-expanded data units (e.g., pixels added between the original pixels) may be input to a neural network or machine-learning model and output a pseudo replica sample picture with dummy values assigned to pixels between the original pixels based on a set of interpolation rules. As a nonlimiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, computing device, processor 112, and/or machine-learning module 300 may utilize sample expander methods, a low-pass filter, or both. For the purposes of this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 112, and/or machine-learning module 300 may use averaging, such as luma or chroma averaging in images, to fill in data units in between original data units.

With continued reference to FIG. 3, in one or more embodiments, computing device, processor 112, and/or machine-learning module 300 may downsample elements of a training example to a desired lower number of data elements. As a nonlimiting example, a high pixel count image may contain 256 pixels, however a desired number of pixels may be 128. Processor 112 may downsample the high pixel count image to convert 256 pixels into 128 pixels. In one or more embodiments, processor 112 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 3, feature selection may include narrowing and/or filtering training data 304 to exclude features and/or elements, or training data including such elements that are not relevant to a purpose for which a trained machine-learning model and/or algorithm is being trained, and/or collection of features, elements, or training data including such elements based on relevance to or utility for an intended task or purpose for which a machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max}-X_{min}$, in the set or subset: $X_{new}=$ $$\frac{X-X_{min}}{X_{max}-X_{min}}.$$

Feature scaling may include mean normalization, wherein a difference between each value, X, and a mean value of a set and/or subset of values, $X_{mean}$, is divided by a range of values, $X_{max}-X_{min}$, in the set or subset:

$$X_{new}=\frac{X-X_{mean}}{X_{max}-X_{min}}.$$

Feature scaling may include standardization, wherein a difference between X and $X_{mean}$ is divided by a standard deviation, $\sigma$, of a set or subset of values:

$$X_{new}=\frac{X-X_{mean}}{\sigma}.$$

Feature scaling may be performed using a median value of a set or subset, $X_{median}$, and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 3, computing device, processor 112, and/or machine-learning module 300 may be configured to perform one or more processes of data augmentation. For the purposes of this disclosure, "data augmentation" is a process that adds data to a training data 304 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 3, machine-learning module 300 may be configured to perform a lazy learning process and/or protocol 320. For the purposes of this disclosure, a "lazy learning" process and/or protocol is a process whereby machine learning is conducted upon receipt of input 312 to be converted to output 308 by combining the input 312 and training data 304 to derive the algorithm to be used to produce the output 308 on demand. A lazy learning process may alternatively be referred to as a "lazy loading" or "call-when-needed" process and/or protocol. For instance, an initial set of simulations may be performed to cover an initial heuristic and/or "first guess" at an output 308 and/or relationship. As a nonlimiting example, an initial heuristic may include a ranking of associations between inputs 312 and elements of training data 304. Heuristic may include selecting some number of highest-ranking associations and/or training data 304 elements. Lazy learning may implement any suitable lazy learning algorithm, including without limitation a k-nearest neighbors algorithm, a lazy naive Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine-learning algorithms as described in further detail below.

With continued reference to FIG. 3, alternatively, or additionally, machine-learning processes as described in this disclosure may be used to generate machine-learning models 324. A "machine-learning model", for the purposes of this disclosure, is a data structure representing and/or instantiating a mathematical and/or algorithmic representation of a relationship between inputs 312 and outputs 308, generated using any machine-learning process including without limitation any process described above, and stored in memory. An input 312 is submitted to a machine-learning model 324 once created, which generates an output 308 based on the relationship that was derived. For instance, and without limitation, a linear regression model, generated using a linear regression algorithm, may compute a linear combination of input data using coefficients derived during machine-learning processes to calculate an output datum. As a further nonlimiting example, a machine-learning model 324 may be generated by creating an artificial neural network, such as a convolutional neural network comprising an input layer of nodes, one or more intermediate layers, and an output layer of nodes. Connections between nodes may be created by "training" the network, in which elements from a training data 304 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 3, machine-learning module 300 may perform at least a supervised machine-learning process 328. For the purposes of this disclosure, a "supervised" machine-learning process is a process with algorithms that receive training data 304 relating one or more inputs 312 to one or more outputs 308, and seek to generate one or more data structures representing and/or instantiating one or more mathematical relations relating input 312 to output 308, where each of the one or more mathematical relations is optimal according to some criterion specified to the algorithm using some scoring function. For instance, a supervised learning algorithm may include inputs 312 described above as inputs, and outputs 308 described above as outputs, and a scoring function representing a desired form of relationship to be detected between inputs 312 and outputs 308. Scoring function may, for instance, seek to maximize the probability that a given input 312 and/or combination thereof is associated with a given output 308 to minimize the probability that a given input 312 is not associated with a given output 308. Scoring function may be expressed as a risk function representing an "expected loss" of an algorithm relating inputs 312 to outputs 308, where loss is computed as an error function representing a degree to which a prediction generated by the relation is incorrect when compared to a given input-output pair provided in training data 304. Supervised machine-learning processes may include classification algorithms as defined above. A person of ordinary skill in the art, upon reviewing the entirety of this disclosure, will be aware of various possible variations of at least a supervised machine-learning process 328 that may be used to determine a relation between inputs and outputs.

With continued reference to FIG. 3, training a supervised machine-learning process may include, without limitation, iteratively updating coefficients, biases, and weights based on an error function, expected loss, and/or risk function. For instance, an output 308 generated by a supervised machine-learning process 328 using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 304 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

With continued reference to FIG. 3, a computing device, processor 112, and/or machine-learning module 300 may be configured to perform method, method step, sequence of method steps, and/or algorithm described in reference to this figure, in any order and with any degree of repetition. For instance, computing device, processor 112, and/or machine-learning module 300 may be configured to perform a single step, sequence, and/or algorithm repeatedly until a desired or commanded outcome is achieved; repetition of a step or a sequence of steps may be performed iteratively and/or recursively using outputs 308 of previous repetitions as inputs 312 to subsequent repetitions, aggregating inputs 312 and/or outputs 308 of repetitions to produce an aggregate result, reduction or decrement of one or more variables such as global variables, and/or division of a larger processing task into a set of iteratively addressed smaller processing tasks. A computing device, processor 112, apparatus 100, or machine-learning module 300 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 3, machine-learning process may include at least an unsupervised machine-learning process 332. For the purposes of this disclosure, an unsupervised machine-learning process is a process that derives inferences in datasets without regard to labels. As a result, an unsupervised machine-learning process 332 may be free to discover any structure, relationship, and/or correlation provided in the data. Unsupervised processes 332 may not require a response variable, may be used to find interesting patterns and/or inferences between variables, to determine a degree of correlation between two or more variables, or the like.

With continued reference to FIG. 3, machine-learning module 300 may be designed and configured to create machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naive Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

With continued reference to FIG. 3, a machine-learning model and/or process may be deployed or instantiated by incorporation into a program, apparatus, system, and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 312 and/or output 308 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine-learning model and/or algorithm may receive inputs 312 from any other process, module, and/or component described in this disclosure, and produce outputs 308 to any other process, module, and/or component described in this disclosure.

With continued reference to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively, or additionally, retraining, deployment, and/or instantiation may be event-based, and may be triggered, without limitation, by user inputs indicating sub-optimal or otherwise problematic performance and/or by automated field testing and/or auditing processes, which may compare outputs 308 of machine-learning models and/or algorithms, and/or errors and/or error functions thereof, to any thresholds, convergence tests, or the like, and/or may compare outputs 308 of processes described herein to similar thresholds, convergence tests or the like. Event-based retraining, deployment, and/or instantiation may alternatively, or additionally, be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data 304 may include, without limitation, training examples including inputs 312 and correlated outputs 308 used, received, and/or generated from any version of any system, module, machine-learning model or algorithm, apparatus, and/or method described in this disclosure. Such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs 308 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 3, one or more processes or algorithms described above may be performed by at least a dedicated hardware unit 336. For the purposes of this disclosure, a "dedicated hardware unit" is a hardware component, circuit, or the like, aside from a principal control circuit and/or processor 112 performing method steps as described in this disclosure, that is specifically designated or selected to perform one or more specific tasks and/or processes described in reference to this figure. Such specific tasks and/or processes may include without limitation pre-processing and/or sanitization of training data and/or training a machine-learning algorithm and/or model. Dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipe-lining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 336 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, processor 112, apparatus 100, or machine-learning module 300 may be configured to instruct one or more dedicated hardware units 336 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 4:
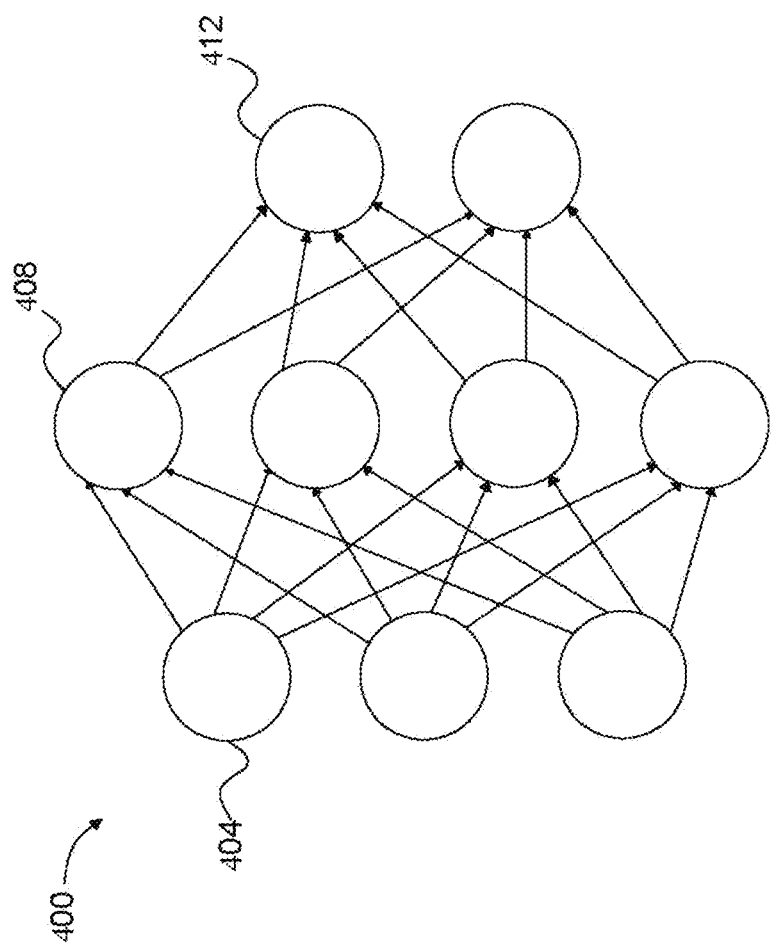
FIG. 4 is a block diagram of an exemplary embodiment of a neural network.

Referring now to FIG. 4, an exemplary embodiment of neural network 400 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 404, at least an intermediate layer of nodes 408, and an output layer of nodes 412. Connections between nodes may be created via the process of "training" neural network 400, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 400 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 400 may include a convolutional neural network comprising an input layer of nodes 404, one or more intermediate layers of nodes 408, and an output layer of nodes 412. For the purposes of this disclosure, a "convolutional neural network" is a type of neural network 400 in which at least one hidden layer is a convolutional layer that convolves inputs to that layer with a subset of inputs known as a "kernel", along with one or more additional layers such as pooling layers, fully connected layers, and the like.

Figure 5:
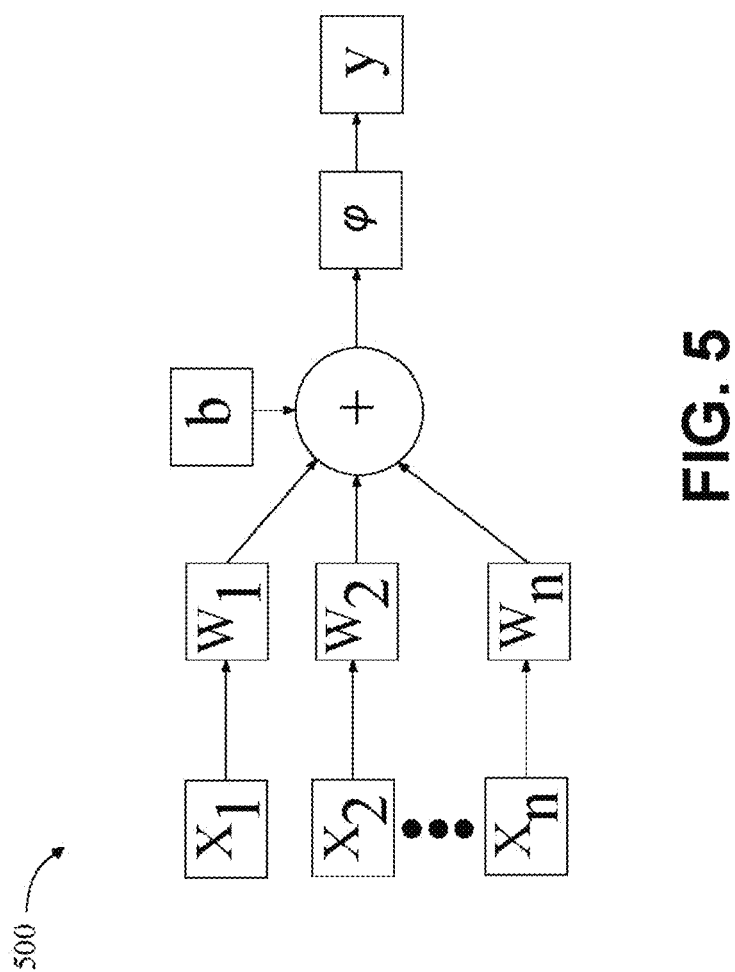
FIG. 5 is a block diagram of an exemplary embodiment of a node of a neural network.

Referring now to FIG. 5, an exemplary embodiment of a node 500 of neural network 400 is illustrated. Node 500 may include, without limitation, a plurality of inputs, $x_i$, that may receive numerical values from inputs to neural network 400 containing the node 500 and/or from other nodes 500. Node 500 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1 - e^{-x}}$$

given input x, a tanh (hyperbolic tangent) function of the form $$\frac{e^x - e^{-x}}{e^x + e^{-x}},$$

a tanh derivative function such as $f(x) = \tanh^2(x)$, a rectified linear unit function such as $f(x) = \max(0,x)$, a "leaky" and/or "parametric" rectified linear unit function such as $f(x) = \max(ax,x)$ for some value of a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x*\text{sigmoid}(x)$, a Gaussian error linear unit function such as $f(x) = a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$, that may be used as activation functions. As a nonlimiting and illustrative example, node 500 may perform a weighted sum of inputs using weights, $w_i$, that are multiplied by respective inputs, $x_i$. Additionally, or alternatively, a bias b may be added to the weighted sum of the inputs such that an offset is added to each unit in a neural network layer that is independent of the input to the layer. The weighted sum may then be input into a function, q, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 400 using training data, which may be performed using any suitable process as described above.

Figure 6:
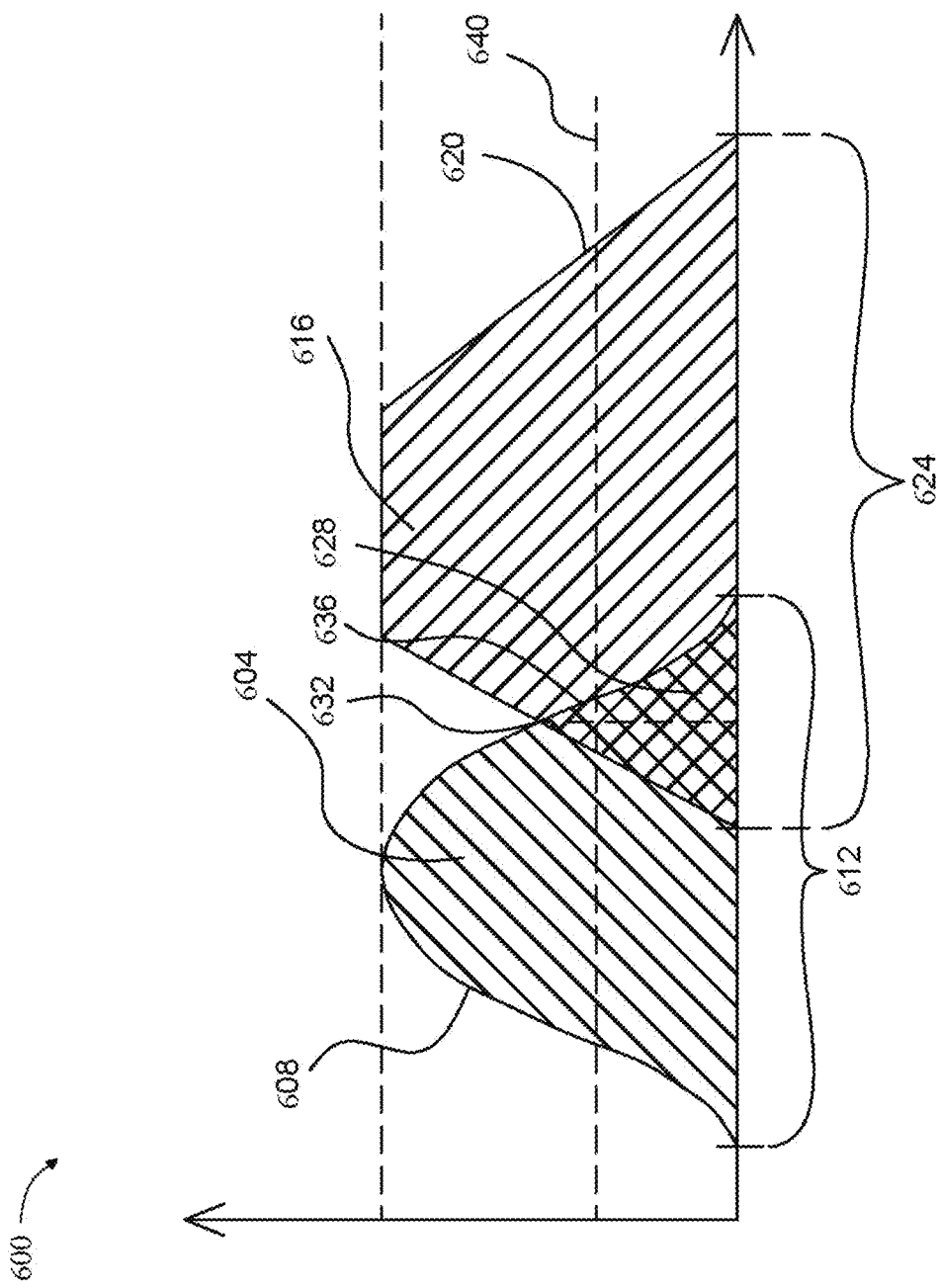
FIG. 6 is an illustration of an exemplary embodiment of fuzzy set comparison.

Referring now to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within the first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range of values 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

A person of ordinary skill in the art, upon reviewing the entirety of this disclosure, will be aware of various alternative or additional membership functions that may be used consistently with this disclosure.

With continued reference to FIG. 6, in one or more embodiments, first fuzzy set 604 may represent any value or combination of values as described above, including output from one or more machine-learning models. A second fuzzy set 616, which may represent any value which may be represented by first fuzzy set 604, may be defined by a second membership function 620 on a second range 624; second range 624 may be identical and/or overlap with first range of values 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range of values 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a nonlimiting example, represent a degree of match between first fuzzy set 604 and second fuzzy set 616, and/or single values therein with each other or with either set, which is sufficient for purposes of the matching process; for instance, threshold 640 may indicate a sufficient degree of overlap between an output from one or more machine-learning models. Alternatively, or additionally, each threshold 640 may be tuned by a machine learning and/or statistical process, for instance and without limitation as described in further detail in this disclosure.

With continued reference to FIG. 6, in one or more embodiments, a degree of match between fuzzy sets may be used to identify one or more matching third-party data structures 108, as described above in this disclosure. As a nonlimiting example, if one or more overlaps are associated with a fuzzy set that matches a fuzzy set of a cohort (e.g., a cohort of matching thresholds 184) by having a degree of overlap exceeding a threshold, computing device may classify the one or more overlaps as belonging to that cohort.

Where multiple fuzzy matches are performed, degrees of match for each respective fuzzy set may be computed and aggregated through, for instance, addition, averaging, or the like, to determine an overall degree of match.

With continued reference to FIG. 6, in one or more embodiments, one or more overlaps may be compared to multiple fuzzy sets of multiple cohorts. As a nonlimiting example, one or more overlaps may be represented by a fuzzy set that is compared to each of the multiple fuzzy sets of multiple cohorts (e.g., cohorts of matching thresholds 184), and a degree of overlap exceeding a threshold between the fuzzy set representing the one or more overlaps and any of the multiple fuzzy sets representing multiple cohorts (e.g., cohorts of matching thresholds 184) may cause computing device to classify the one or more overlaps as belonging to that cohort. As a nonlimiting example, there may be two fuzzy sets representing two cohorts, cohort A and cohort B. Cohort A may have a cohort A fuzzy set, cohort B may have a cohort B fuzzy set, and one or more overlaps may have a overlap fuzzy set. Computing device may compare overlap fuzzy set with each of cohort A fuzzy set and cohort B fuzzy set, as described above, and classify the overlap fuzzy set to either, both, or neither of cohort A fuzzy set and cohort B fuzzy set. Machine-learning methods as described throughout this disclosure may, in a nonlimiting example, generate coefficients used in fuzzy set equations as described above, such as without limitation x, c, and σ of a Gaussian set as described above, as outputs of machine learning methods. Likewise, overlaps may be used indirectly to determine a fuzzy set, as overlap fuzzy set may be derived from outputs of one or more machine-learning models that take overlaps directly or indirectly as inputs.

With continued reference to FIG. 6, in one or more embodiments, fuzzy set comparison 600 may include a fuzzy inference model. For the purposes of this disclosure, a "fuzzy inference model" is a model that uses fuzzy logic to reach a decision and derive a meaningful outcome. As a nonlimiting example, a fuzzy inference system may be associated with various degrees of match, as described above. In one or more embodiments, an inferencing rule may be applied to determine a fuzzy set membership of a combined output based on the fuzzy set membership of linguistic variables. As a nonlimiting example, membership of a combined output in a "medium-level match" fuzzy set may be determined based on a percentage membership of a second linguistic variable with a first mode in the "medium-level match" fuzzy set and a percentage membership of the second linguistic variable associated with a second mode in a "upper-medium-level match" fuzzy set. In one or more embodiments, parameters of overlaps may then be determined by comparison to a threshold or output using another defuzzification process. Each stage of such a process may be implemented using any type of machine-learning model, such as any type of neural network, as described herein. In one or more embodiments, parameters of one or more fuzzy sets may be tuned using machine learning. In one or more embodiments, fuzzy inferencing and/or machine learning may be used to synthesize an overall output (e.g., overlap score 164) from individual outputs (e.g., overlaps). In some cases, outputs may be combined to make an overall or final determination, which may be displayed with or instead of individual outputs. As another nonlimiting example, outputs may be ranked, wherein the output with the highest confidence score may be the output displayed at display device or displayed first in a ranked display of result outputs.

With continued reference to FIG. 6, fuzzy set comparison 600 may be generated as a function of determining a data compatibility threshold. Data compatibility threshold may be determined by a computing device. In some embodiments, computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine learning, or other method that may occur to a person of ordinary skill in the art upon reviewing the entirety of this disclosure. In some embodiments, determining compatibility threshold may include using a linear regression model. A linear regression model may include a machine-learning model. In some embodiments, determining compatibility threshold may include using a classification model. A classification model may be configured to input collected data and cluster data to a centroid based on, but not limited to, frequency of appearance, linguistic indicators of compatibility and/or allowability, and the like. Centroids may include scores assigned to them such that the compatibility threshold may each be assigned a score. In some embodiments, a classification model may include a k-means clustering model. In some embodiments, a classification model may include a particle swarm optimization model. In some embodiments, determining a compatibility threshold may include using a fuzzy inference engine. A fuzzy inference engine may be configured to map one or more compatibility thresholds using fuzzy logic. In some embodiments, a plurality of computing devices may be arranged by a logic comparison program into compatibility arrangements. Membership function coefficients and/or constants as described above may be tuned according to classification and/or clustering algorithms. As a nonlimiting example, a clustering algorithm may determine a Gaussian or other distribution about a centroid corresponding to a given compatibility threshold, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

With continued reference to FIG. 6, an inference engine may combine rules, such as any semantic language and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), associativity: T(a, T(b, c))=T(T(a, b), c), and the requirement that the number 1 acts as an identity element. Combinations of rules ("and" or "or" combination of rule membership determinations) may be performed using any T-conorm, as represented by an inverted T symbol or "⊥", such as max (a, b), probabilistic sum of a and b (a+b−a×b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally, T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

Figure 7:
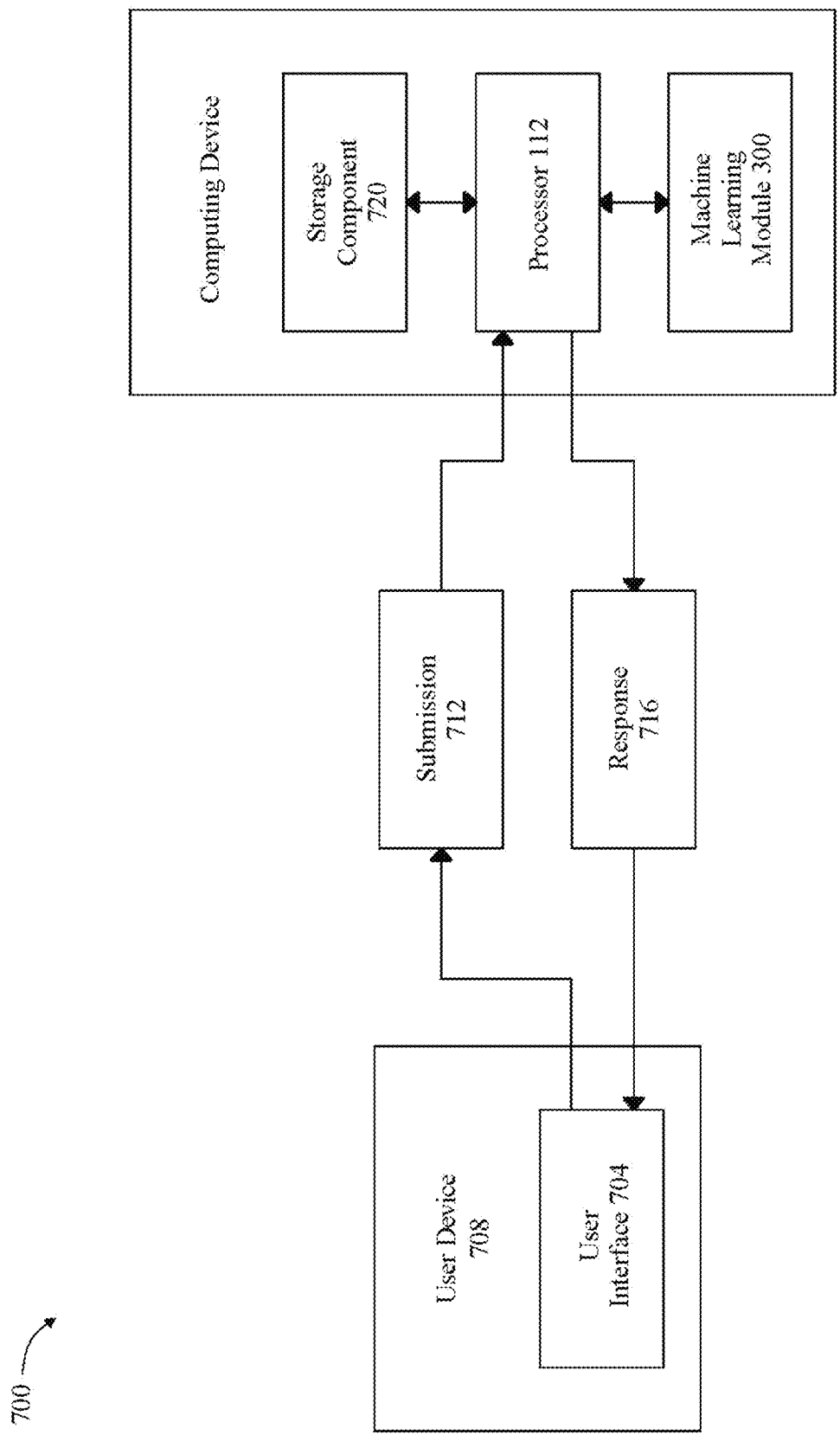
FIG. 7 is an exemplary embodiment of a chatbot system.

Referring now to FIG. 7, in one or more embodiments, apparatus 100 may perform one or more of its functions, such as receiving user data 104, by implementing at least a chatbot system 700, an exemplary embodiment of which is schematically illustrated. In one or more embodiments, a user interface 704 may be communicatively connected with a computing device that is configured to operate a chatbot. In some cases, user interface 704 may be local to computing device. Alternatively, or additionally, in some other cases, user interface 704 may be remote to computing device, e.g., as part of a user device 708, and communicative with the computing device and processor 112 therein, by way of one or more networks, such as without limitation the internet. Alternatively, or additionally, user interface 704 may communicate with user interface 704 and/or computing device using telephonic devices and networks, such as without limitation fax machines, short message service (SMS), or multimedia message service (MMS). Commonly, user interface 704 may communicate with computing device using text-based communication, for example without limitation using a character encoding protocol, such as American Standard for Information Interchange (ASCII). Typically, user interface 704 may conversationally interface a chatbot, by way of at least a submission 712, from the user interface 704 to the chatbot, and a response 716, from the chatbot to the user interface 704. In many cases, one or both of submission 712 and response 716 are text-based communication. Alternatively, or additionally, in some cases, one or both of submission 712 and response 716 are audio-based communication.

With continued reference to FIG. 7, submission 712, once received by user interface 704 and/or computing device that operates a chatbot, may be processed by processor 112. In one or more embodiments, processor 112 may process submission 712 using one or more of keyword recognition, pattern matching, and natural language processing. In one or more embodiments, processor 112 may employ real-time learning with evolutionary algorithms. In one or more embodiments, processor 112 may retrieve a pre-prepared response from at least a storage component 720, based upon submission 712. Alternatively, or additionally, in one or more embodiments, processor 112 may communicate a response 716 without first receiving a submission 712, thereby initiating a conversation. In some cases, processor 112 may communicate an inquiry to user interface 704 and/or computing device, wherein processor 112 is configured to process an answer to the inquiry in a following submission 712 from the user interface 704 and/or computing device. In some cases, an answer to an inquiry presented within submission 712 from user interface 704 and/or computing device may be used by the computing device as an input to another function.

Figure 8:
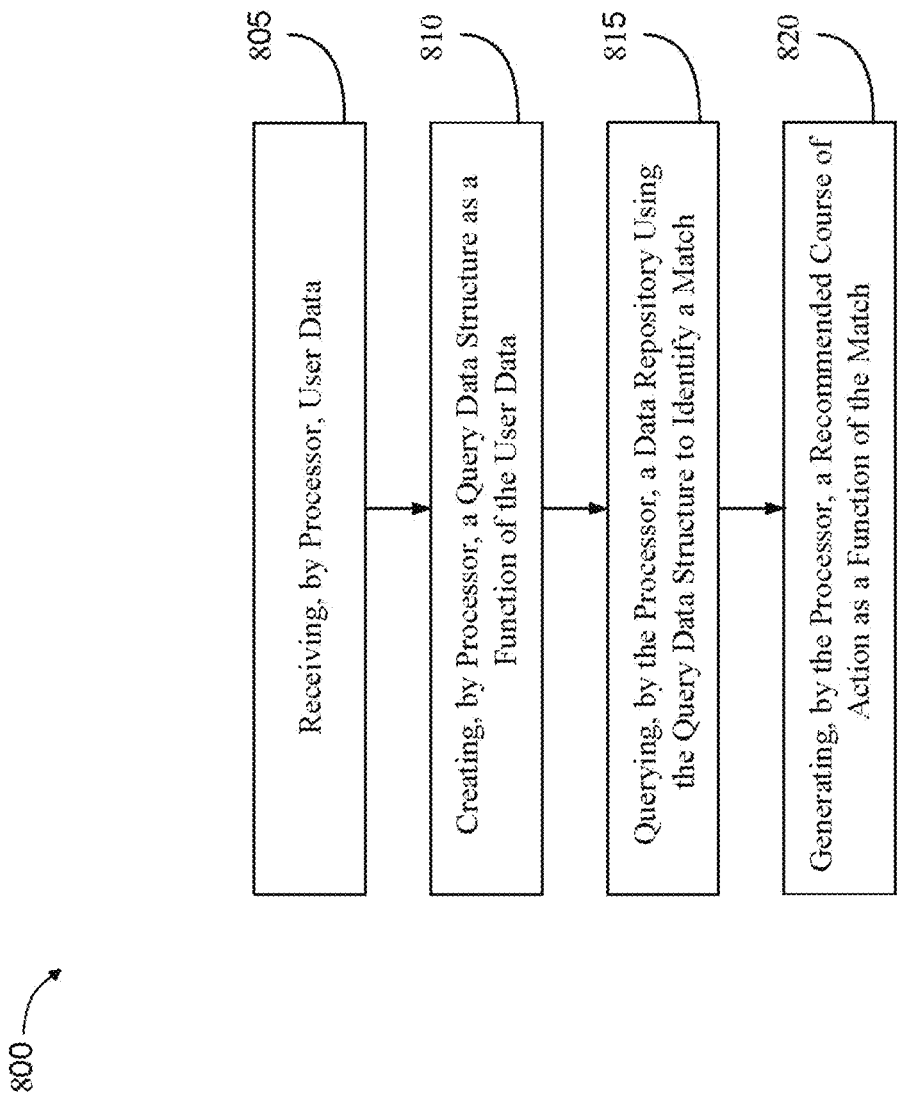
FIG. 8 is an exemplary flow diagram illustrating a method for matching user data with third-party data structures.

Referring now to FIG. 8, an exemplary embodiment of a method 800 for matching user data 104 with third-party data structures 108 is described. At step 805, method 800 includes receiving, by at least a processor 112, user data 104.

This step may be implemented with reference to details described above in this disclosure and without limitation.

With continued reference to FIG. 8, at step 810, method 800 includes creating, by at least a processor 112, a query data structure 120 as a function of user data 104, the query data structure 120 including a query attribute 124 and a first temporal attribute 128. This step may be implemented with reference to details described above in this disclosure and without limitation.

With continued reference to FIG. 8, at step 815, method 800 includes querying, by at least a processor 112, a data repository 148 using query data structure 120 to identify one or more matches. Data repository 148 includes a plurality of third-party data structures 108, wherein each third-party data structure 108 of the plurality of third-party data structures 108 includes at least a data feature 152 and a second temporal attribute 156. Identifying the one or more matches includes computing a first overlap 168a as a function of query attribute 124 and data feature 152, computing a second overlap 168b as a function of first temporal attribute 128 and second temporal attribute 156, and computing an overlap score 164 as a function of the first overlap 168a, a first weight 172a associated with the first overlap 168a, the second overlap 168b, and a second weight 172b associated with the second overlap 168. Identifying the one or more matches further includes comparing overlap score 164 with one or more matching thresholds 184. This step may be implemented with reference to details described above in this disclosure and without limitation.

With continued reference to FIG. 8, at step 820, method 800 includes generating, by at least a processor 112, a recommended course of action 192 as a function of the one or more matches. This step may be implemented with reference to details described above in this disclosure and without limitation.

Figure 9:
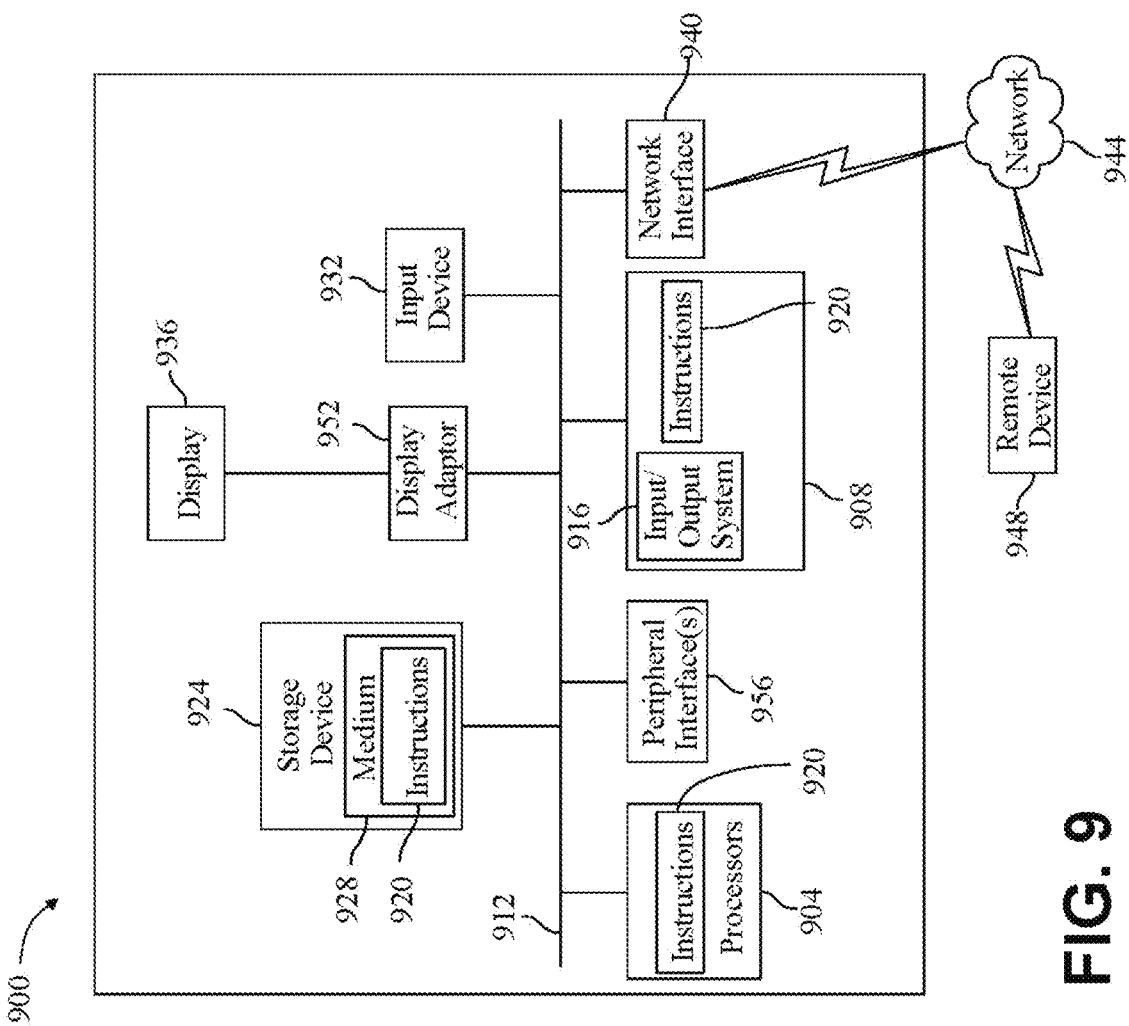
FIG. 9 is a block diagram of an exemplary embodiment of a computing system that can be used to implement any one or more of the methodologies disclosed herein and any one or more portions thereof.

Referring now to FIG. 9, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 9, the figure shows a diagrammatic representation of one embodiment of a computing device in the exemplary form of a computing system 900 within which a set of instructions for causing the computing system 900 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 900 may include a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures. Processor 904 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 9, memory 908 may include various components (e.g., machine-readable media) including, but not limited to, a random-access memory component, a read only component, and any combinations thereof. In one example, a basic input/output system 916, including basic routines that help to transfer information between elements within computing system 900, such as during start-up, may be stored in memory 908. Memory 908 (e.g., stored on one or more machine-readable media) may also include instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

With continued reference to FIG. 9, computing system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 924 (or one or more components thereof) may be removably interfaced with computing system 900 (e.g., via an external port connector (not shown)). Particularly, storage device 924 and an associated machine-readable medium 928 may provide nonvolatile and/or volatile storage of machine-readable instructions, data structures, program modules, and/or other data for computing system 900. In one example, software 920 may reside, completely or partially, within machine-readable medium 928. In another example, software 920 may reside, completely or partially, within processor 904.

With continued reference to FIG. 9, computing system 900 may also include an input device 932. In one example, a user of computing system 900 may enter commands and/or other information into computing system 900 via input device 932. Examples of input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display device 936, discussed further below. Input device 932 may be utilized as a user selection device for selecting one or more graphical representations in a graphical interface as described above.

With continued reference to FIG. 9, user may also input commands and/or other information to computing system 900 via storage device 924 (e.g., a removable disk drive, a flash drive, etc.) and/or network interface device 940. A network interface device, such as network interface device 940, may be utilized for connecting computing system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computing system 900 via network interface device 940.

With continued reference to FIG. 9, computing system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Video display adapter 952 and display device 936 may be utilized in combination with processor 904 to provide graphical representations of aspects of the present disclosure. In addition to a display device, computing system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for matching user data with third-party data structures, the apparatus comprising:
    at least a processor; and
    a memory communicatively connected to the at least a processor, wherein the memory comprises instructions configuring the at least a processor to:
        receive user data;
        create a query data structure as a function of the user data, the query data structure comprising at least a query attribute and a first temporal attribute, wherein creating the query data structure comprises:
            receive content retrieval training data comprising plurality of exemplary query data structures as outputs correlated with a plurality of exemplary user data as inputs;
            iteratively training a content retrieval machine-learning model using the content retrieval training data; and creating the query data structure using the content retrieval machine-learning model;
query a data repository using the query data structure to identify one or more matches, wherein:
the data repository comprises a plurality of third-party data structures, wherein each third-party data structure of the plurality of third-party data structures comprises at least a data feature and a second temporal attribute; and
identifying the one or more matches comprises:
computing a first overlap as a function of the at least a query attribute and the at least a data feature;
computing a second overlap as a function of the first temporal attribute and the second temporal attribute;
computing an overlap score as a function of the first overlap, a first weight associated with the first overlap, the second overlap, and a second weight associated with the second overlap; and
identifying the one or more matches by comparing the overlap score with one or more matching thresholds; and
generate a recommended course of action as a function of the one or more matches.

2. The apparatus of claim 1, wherein:
the query data structure further comprises a first positional attribute;
each third-party data structure of the plurality of third-party data structures further comprises a second positional attribute; and
identifying the one or more matches further comprises:
computing a third overlap as a function of the first positional attribute and the second positional attribute; and
computing the overlap score as a function of the third overlap and a third weight associated with the third overlap.

3. The apparatus of claim 1, wherein the content retrieval machine-learning model comprises a large language model (LLM) trained on a plurality of training examples and configured to extract text-based data, wherein training the LLM comprises:
pretraining the LLM on a general set of training examples; and
retraining the LLM on a special set of training examples, wherein the general and the special set of training examples are subsets of the plurality of training examples.

4. The apparatus of claim 1, wherein computing the overlap score comprises:
receiving overlap calculation training data comprising a plurality of exemplary overlap scores as outputs correlated with a plurality of exemplary query data structures as inputs;
iteratively training an overlap calculation machine-learning model using the overlap calculation training data by adjusting a plurality of weights; and
computing the overlap score as a function of the overlap calculation machine-learning model.

5. The apparatus of claim 1, wherein:
each third-party data structure of the plurality of third-party data structures is associated with a positivity metric; and
identifying the one or more matches comprises:
filtering the plurality of third-party data structures as a function of the positivity metric; and
updating the one or more matches as a function of the filtered plurality of third-party data structures.

6. The apparatus of claim 1, wherein at least a third-party data structure of the plurality of third-party data structures comprises a clinical trial program.

7. The apparatus of claim 1, wherein the recommended course of action comprises a treatment plan.

8. The apparatus of claim 1, wherein querying the data repository includes identifying one or more prior users associated with at least a third-party data structure of the plurality of third-party data structures.

9. The apparatus of claim 1, wherein the processor is further configured to:
receive secondary user data;
modify the query data structure as a function of the secondary user data; and
update the data repository as a function of the modified query data structure.

10. A method for matching user data with third-party data structures, the method comprising:
receiving, by at least a processor, user data;
creating, by the at least a processor, a query data structure as a function of the user data, the query data structure comprising at least a query attribute and a first temporal attribute, wherein creating the query data structure comprises:
receiving, by the at least a processor, content retrieval training data comprising a plurality of exemplary query data structures as outputs correlated with a plurality of exemplary user data as inputs;
iteratively, by the at least a processor, training a content retrieval machine-learning model using the content retrieval training data; and
creating, by the at least a processor, the query data structure using the content retrieval machine-learning model;
querying, by the at least a processor, a data repository using the query data structure to identify one or more matches, wherein:
the data repository comprises a plurality of third-party data structures, wherein each third-party data structure of the plurality of third-party data structures comprises at least a data feature and a second temporal attribute; and
identifying the one or more matches comprises:
computing a first overlap as a function of the at least a query attribute and the at least a data feature;
computing a second overlap as a function of the first temporal attribute and the second temporal attribute;
computing an overlap score as a function of the first overlap, a first weight associated with the first overlap, the second overlap, and a second weight associated with the second overlap; and
identifying the one or more matches by comparing the overlap score with one or more matching thresholds; and
generating, by the at least a processor, a recommended course of action as a function of the one or more matches.

11. The method of claim 10, wherein:
the query data structure further comprises a first positional attribute;
each third-party data structure of the plurality of third-party data structures further comprises a second positional attribute; and identifying the one or more matches further comprises:
  computing a third overlap as a function of the first positional attribute and the second positional attribute; and
  computing the overlap score as a function of the third overlap and a third weight associated with the third overlap.

12. The method of claim 10, wherein the content retrieval machine-learning model comprises a large language model (LLM) trained on a plurality of training examples and configured to extract text-based data, wherein training the LLM comprises:
  pretraining the LLM on a general set of training examples; and
  retraining the LLM on a special set of training examples, wherein the general and the special set of training examples are subsets of the plurality of training examples.

13. The method of claim 10, wherein computing the overlap score comprises:
  receiving overlap calculation training data comprising a plurality of exemplary overlap scores as outputs correlated with a plurality of exemplary query data structures as inputs;
  iteratively training an overlap calculation machine-learning model using the overlap calculation training data by adjusting a plurality of weights; and
  computing the overlap score as a function of the overlap calculation machine-learning model.

14. The method of claim 10, wherein:
  each third-party data structure of the plurality of third-party data structures is associated with a positivity metric; and
  identifying the one or more matches comprises:
    filtering the plurality of third-party data structures as a function of the positivity metric; and
    updating the one or more matches as a function of the filtered plurality of third-party data structures.

15. The method of claim 10, wherein at least a third-party data structure of the plurality of third-party data structures comprises a clinical trial program.

16. The method of claim 10, wherein the recommended course of action comprises a treatment plan.

17. The method of claim 10, wherein querying the data repository includes identifying one or more prior users associated with at least a third-party data structure of the plurality of third-party data structures.

18. The method of claim 10, further comprising:
  receiving, by the at least a processor, secondary user data;
  modifying, by the at least a processor, the query data structure as a function of the secondary user data; and
  updating, by the at least a processor, the data repository as a function of the modified query data structure.

\* \* \* \* \*